United States Patent [19] | [11] Patent Number: 5,011,494
von Recum et al. | [45] Date of Patent: Apr. 30, 1991

[54] SOFT TISSUE IMPLANT WITH MICRON-SCALE SURFACE TEXTURE TO OPTIMIZE ANCHORAGE

[75] Inventors: Andreas F. von Recum, Six Mile, S.C.; Craig E. Campbell, Ridley Park, Pa.

[73] Assignee: Clemson University, Clemson, S.C.

[21] Appl. No.: 511,555

[22] Filed: Apr. 20, 1990

Related U.S. Application Data

[63] Continuation of Ser. No. 245,763, Sep. 16, 1988, abandoned.

[51] Int. Cl.$^5$ ............... A61F 2/02; A61F 2/06; A61F 2/12; A61F 2/24
[52] U.S. Cl. ............... 623/11; 623/1; 623/2; 623/8; 600/36
[58] Field of Search ............... 623/1, 8, 11, 12, 66, 623/2, 13, 17; 600/36

[56] References Cited

U.S. PATENT DOCUMENTS 4,011,861  3/1977  Enger .
4,321,711  3/1982  Mano .
4,374,889  2/1983  MacGregor .
4,822,361  4/1989  Okita et al. .

OTHER PUBLICATIONS

Boyce, Biologic and Synthetic Vascular Prostheses, "Physical Characteristics of Expanded Polytetrafluoroethylene Grafts", pp. 553–561 (1982), FIGS. 33-2 and 33-3.
Campbell et al., Surgery, "Expanded Microporous Polytetrafluoroethylene as a Vascular Substitute: A Two Year Follow-up," vol. 85, pp. 177–183 (1979), FIG. 1A.
Campbell et al., Annals of Surgery, "A Small Arterial Substitute, Expanded Microporous Polytetrafluoroethylene: Patency Versus Porosity", vol. 182, pp. 138–143 (1975), FIG. 1.
Kester, Biomat., Med. Dev., Art. Org., "Reinforced Expanded Polytetrafluoroethylene (Gore-Tex) Grafts for Haemodialysis", vol. 6, No. 4, pp. 331–340 (1978), FIG. 2.
Squier et al., "The Relationship Between Soft Tissue Attachment, Epithelial Downgrowth, and Surface Porosity", Journal Periodontal Research, vol. 16, pp. 434–440, 1981.
Schreuders et al., "Normal Wound Healing Compared to Healing Within Porous Dacron Implants", J. Biomed, Mat. Res., vol. 22, pp. 121–135 (1988).
Wasfie et al., "Inhibition of Epithelial Downgrowth on Percutaneous Access in Swine: II", vol. XXX, Trans Am Soc Artif Intern Organs, pp. 556–560 (1984).
Freed et al., "Long-term Percutaneous Access Device", vol. XXXI, Trans Am Soc Artif Intern Organs, pp. 230–232 (1985).
Chehroudi et al., "Effects of a Grooved Epoxy Substratum on Epithelial Cell Behavior in Vitro and in Vivo", Journal of BioMedical Materials Research, vol. 22, pp. 459–473 (1988).
Eskin et al., "Endothelial Cell Culture on Dacron Fabrics of Different Configurations", J. Biomed. Mat. Res., vol. 12, pp. 517–524 (1978).

Primary Examiner—Alan W. Cannon
Attorney, Agent, or Firm—Dority & Manning

[57] ABSTRACT

A soft tissue implant device such as a catheter, heart valve, or plastic or reconstructive surgical material, to be at least partially embedded in an implantation site in soft organic tissue of a living organism includes a body defining a surface layer extending over the portion of the body contacting the organic tissue. The surface layer defines a three-dimensional pattern with an exterior surface defining a plurality of spaces and a plurality of solid surface portions. The spaces have a mean bridging distance ranging from greater than 1.0 micron to less than 4.0 microns and the solid surfaces portions have mean breadths ranging from 0.10 micron to 2.0 microns. The mean bridging distance is preferably greater than 1.4 microns and less than 1.9 microns. The exterior surface is substantially free of indentations having a bridging distance measuring in a range from between 10.0 microns and 1,000 microns.

10 Claims, 10 Drawing Sheets

SOFT TISSUE IMPLANT WITH MICRON-SCALE SURFACE TEXTURE TO OPTIMIZE ANCHORAGE

This is a continuation of application Ser. No. 07/245,763, filed Sept. 16, 1988 now abandoned.

BACKGROUND OF THE INVENTION

The invention relates to soft tissue implants and more particularly to soft tissue implants with a micron-scale surface texture to optimize anchorage of the implant in the tissue bed.

The reaction of living tissue to an implant can take a number of different forms. For example, the initial response to the surgical trauma of implantation is usually called the acute inflammatory reaction and is characterized by an invasion of polymorphonuclear leukocytes (PMNs). The acute inflammatory reaction is followed by the chronic inflammatory reaction, which is characterized by the presence of numerous macrophages and lymphocytes, some monocytes and granulocytes. Fibroblasts also begin accumulating in the vicinity of the implant and begin producing a matrix of collagen. The macrophages attempt to phagocytize the implant. However, if the implant is too large to be engulfed by the macrophages and is of a material resistant to digestion by the macrophages, these macrophages fuse together to form multinucleate foreign body giant cells, hereafter referred to simply as giant cells. Macrophages and giant cells are the most common type of cell around many types of implants. The fibroblasts and collagen form a connective tissue capsule around the implant and the chronic inflammatory cells to effectively isolate the implant and these cells from the rest of the body. Connective tissue consisting of a fine network of collagen with active producing fibroblasts accompanied by chronic inflammatory cells, capillaries and blood vessels is referred to collectively as granulation tissue.

Thus, when a material is implanted into a soft tissue bed of a living organism such as a human or an animal, a granulation tissue capsule is formed around the implant material consisting of inflammatory cells, immature fibroblasts and blood vessels. This tissue capsule usually increases in thickness with time and contracts around the implant, deforming the implantation site, and possibly the implant itself depending upon the rigidity of the implant.

When an optimally biocompatible material is implanted, it elicits the formation of a thin and stable connective tissue film covering the implant surface with minimal involvement of inflammatory tissue components such as macrophages and giant cells. It is well documented in the biomaterials literature that bulk chemistry, electrochemical surface phenomena, surface geometry, and implant shape are factors determining the local histological response (histocompatibility) in the implantation site.

When the implant is porous with pore entry diameters larger than 20 microns, tissue grows into these pores. This phenomenon appears desirable to many investigators because in theory it allows tissue ingrowth into the implant and reduces capsular contraction. For example, U.S. Pat. No. 4,011,861 to Enger discloses an implantable electric terminal which has pores preferably in the range of about 10 to 500 microns so that blood vessels and tissue can grow into the pores. Similarly, MacGregor (U.S. Pat. No. 4,374,699) discloses a rigid implant having pores sized from 1 to 1,000 microns to allow penetration by blood cells. MacGregor also discloses a flexible polymeric implant having pores sized less than 20 microns to allow ingrowth by soft tissue.

However, our analytical studies of the ingrowing tissues revealed granulation tissue in these pores. This granulation tissue consisted of predominately inflammatory cells, relatively few fibroblasts decreasing in number with implantation time, and very immature extracellular connective tissue components. This chronic inflammatory tissue is highly undesirable since it represents a locus minoris resistentiae, and it appears to prevent the formation of mature connective tissue which is the optimal tissue for implant anchorage. See Schreuders et al. "Normal Wound Healing Compared to Healing within Porous Dacron Implants," *J. Biomed. Mat. Res.*, 1988.

*Eskin et al.* "Endothelial Cell Culture on Dacron fabrics of Different Configurations," J. Biomed. Mat. Res., volume 12, pages 517–524 (1978), reports on tests conducted with Dacron knits, velours, and felt, in which the filaments comprising all of the materials were about 10.0 microns in diameter. Endothelial cells appeared unable to bridge spaces between filaments and strands of yarn of greater than 20–30 microns. The bridging occurred only where the strands of yarn were contiguous or nearly so, and the cells did not grow into the interior of the yarn, but stayed on its surface. Moreover, the cells did not grow over each other. It was noted that vascular smooth muscle cells are able to bridge distances between filaments in Dacron velours measuring up to 500 microns. It was suggested that different properties between endothelial cells and smooth muscle cells might account for the different behaviors.

In Wasfie et al, "Inhibition of Epithelial Downgrowth on Percutaneous Access Devices in Swine: II," volume XXX, Trans Am Soc Artif Intern Organs. pages 556–560 (1984) and Freed et al. "Long-term Percutaneous Access Device," volume XXXI, *Trans Am Soc Artif Intern Organs,* pages 230–232 (1985), the researchers describe a Percutaneous Access Device (PAD) designed to form a seal between it and the surrounding tissue to inhibit epidermal downgrowth and prevent resulting infection. The implant neck of the surface of the PAD is rendered "nanoporous," which means according to these researchers that it has pores which average 1.0 micron in diameter and 20 microns in depth. The pores are non-intercommunicating. and are produced at a density of 15,000 per mm$^2$. As shown in FIG. 3a of Wasfie et al, this pore density means that separations between pores can measure ten (10) microns or more. In developing their design for a stable PAD, they sought to inhibit epithelial migration and prevent entry of bacteria by mechanically stabilizing the PAD so as to protect the device-tissue interface from applied forces. The PAD is coated with autologous dermal fibroblasts using cell culture techniques under in vitro conditions that favor fibroblast proliferation followed by in vitro collagen synthesis and polymerization. The in vitro cell culture technique allows the autologous dermal fibroblasts to interlock firmly with the "nanoporous" surface, before the percutaneous implant is surgically inserted in vivo, i.e., into the living organism. The result of the in vitro cell culturing technique on the nanoporous surface is an Autologous, Living, Coated, Nanoporous surface, which is referred to as an ALCON surface. The PAD with the ALCON surface is then implanted in vivo into various living hosts such as swine, sheep, and humans. FIGS. 3a, 3b, and 4 of Wasfie et al show fibroblas cytoplasmic extensions protruding into pores of the "nanoporous" Lexan surface of the PAD neck. The Wasfie et al cytoplasmic researchers believe that these cells are the original fibroblasts used to coat the implant surface in vitro to form the ALCON surface.

As reported in Freed et al. the swine ALCON surface implants had a PAD failure rate of one every 82 implantmonths compared to a control failure rate of one every seven implant-months for PAD implants without the in vitro pre-implantation coating of autologous dermal fibroblasts. According to Freed et al. the failure rate of the ALCON surface implants shows promise as an effective means for transferring pneumatic power to an implanted heart system and as potentially useful for continuous ambulatory peritoneal dialysis and other therapies. However, the implants lacking the in vitro ALCON surface failed far sooner than conventional percutaneous implant devices.

Chehroudi et al. "Effects of a Grooved Epoxy Substratum on Epithelial Cell Behavior in vitro and in vivo." Journal of BioMedical Materials Research, Vol. 22, pp. 459-473 (1988), tested the hypothesis that contact guidance can be used to control epithelial migratory behavior with a study conducted in vitro and in the more complex in vivo environment. Epoxy resin structures having a smooth portion and a portion with V-shaped grooves measuring 10 microns deep, 17 microns across the top, and separated by flat ridges 22 microns wide, were implanted in rats. The report concludes that more epidermal cells attached to the grooved portion of the epoxy substrata than to the smooth portion. The epidermal cells interdigitated into the grooves of the grooved portion of the implant. The report concluded that the grooved substrata used in the study do not decrease and probably increase cell attachment. The absence of interconnecting pores which might facilitate infection was noted as an advantage of the epoxy substrata.

OBJECTS AND SUMMARY OF THE INVENTION

It is the principal object of the present invention to provide an improved soft tissue implant having a surface texture that optimizes anchorage of the implant to the tissue without causing inflammatory tissue at the implantation site.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an implant device structured according to the present invention is intended to be at least partially embedded at an implantation site in organic tissue of a living organism. Accordingly, a device structured in accordance with the present invention comprises an implant device such as the catheter for a pacemaker or for attaching a kidney dialysis machine, heart valves, vascular grafts, and plastic and reconstructive surgical materials. An implant device according to the present invention promotes anchorage of the device at the implantation site and the growth of collagen at the implantation site, without causing encapsulation of the embedded portion of the device and without causing inflammatory tissue to form at the implantation site.

A device structured in accordance with the present invention comprises an implant device having a body that defines a surface layer. The surface layer must extend over a sufficient portion of the body so that only the surface layer comes into contact with the organic tissue at the implantation site.

In further accordance with the present invention, the surface layer defines a three-dimensional pattern. As embodied herein, the surface layer defines a plurality of three dimensional features, including a plurality of recesses and a plurality of projections. Each projection has a side wall that defines at least a portion of at least one adjacent recess, and the recesses and projections are interspersed among each other.

In still further accordance with the present invention, each feature defines a local exterior surface for presenting itself to living cells in organic tissue adjacent the exterior surface at the implantation site. The local exterior surface encompasses and includes a plurality of spaces, and a plurality of solid surface portions. As embodied herein, the exterior surface defines a plurality of spaces which present themselves to the living cells and a plurality of solid surface portions which present themselves to living cells.

In some embodiments, a closed perimeter defines each space in the exterior surface of the surface layer. Such closed perimeter defines the boundary of the opening to the underlying recess. Each space defines the exterior surface of each underlying recess.

In other embodiments, a closed perimeter defines a solid surface portion therewithin. The solid surface portion defines the exterior surface of each projection. Such closed perimeter forms the boundary between the solid surface portion and the spaces which form the remainder of the exterior surface of the surface layer.

In accordance with the present invention, the smallest dimension of the spaces, not the largest, is a limiting factor concerning ingrowth or attachment of cells or cellular products. Accordingly, a bridging distance defines the minimum distance an adjacent cell must stretch to span diametrically across the spaces forming the exterior surface of the surface layer. The bridging distance is measured in a direction parallel to the exterior surface at the space in question. For example, a discrete space having an oval or ellipsoidal perimeter defines a major axis and a minor axis, and the minor axis is the bridging distance. Note that the bridging distance differs from the distance spanned by the major axis of the space.

To be precise, the diametric distance is a line drawn from one side of the perimeter of the space to the other side of the perimeter of the space that also passes through the center of the area bounded by the closed perimeter. However, because the mean bridging distance constitutes the significant measurement for purposes of the present invention and the number of diametric distances used to calculate the mean will be very large, a sight judgment is believed to be adequate for purposes of selecting the bridging distance across any space in the surface of implants having surface layers according to the present invention. However, the sight measurement is made upon magnification of the actual naked eye observation by a microscope, and the magnification should be a minimum of 80 times magnification when making the measurements in question.

For reasons explained more fully below, the mean bridging distance of the plurality of spaces in the exterior surface of the surface layer of implants according to the present invention must fall within the range from greater than 1.0 micron to less than 4.0 microns. Preferably, the range of mean bridging distances should fall within the range of from greater than 1.4 microns to less than 1.9 microns. Thus, the odd space could have a bridging distance that measures less than 1.0 micron or more than 4.0 microns, so long as the mean bridging distance of all of the spaces stays within the 1.0 micron to 4.0 micron range.

In one alternative embodiment of the present invention, a surface layer pattern defines a plurality of discrete projections. For example, a continuum of spaces surrounds a plurality of discrete, i.e., individual and discontinuous, solid surface portions of the exterior surface. Each of the projections extends in a direction normal to the body. The bridging distance is defined as the smallest distance separating the perimeters of the solid surface portions of adjacent projections measured in a direction parallel to the exterior surface. For example, for any given projection, the distance separating the perimeter of its exterior solid surface portion from every adjacent projection's exterior solid surface portion perimeter measured in a direction parallel to the exterior surface is determined, and these distances are the characteristic bridging distances of that particular projection.

As explained hereinafter more fully below, the mean bridging distance of the space surrounding the plurality of solid surface portions in the exterior surface of the surface layer of implants according to the present invention must fall within the range of from greater than 1.0 micron to less than 4.0 microns. Preferably, the range of mean bridging distances should fall within the range of from greater than 1.4 microns to less than 1.9 microns. Thus, the odd solid surface portion could form the boundary of a bridging distance that measures less than 1.0 micron or more than 4.0 microns so long as the mean of all of the bridging distances bounded by the plurality of solid surface portions stays within the 1.0 micron to 4.0 micron range.

Furthermore, each solid surface portion of each projection also has a breadth dimension that is defined as the smallest diametric distance of the exterior surface portion of the projection measured in a direction parallel to the exterior surface portion. The mean breadth of the projections preferably ranges between 0.1 microns to 2.0 microns. Again, because of the large number of measurements involved, a sight selection of the breadth measurement is adequate for purposes of the present invention. However, the sight measurement is made upon magnification of the actual naked eye observation by a microscope, and the magnification should be a minimum of 80 times magnification when making the measurements in question. Again, the odd projection could have a breadth less than 0.1 microns or greater than 2.0 microns so long as the plurality of projections has a mean breadth within the 0.1 micron to 2.0 micron range.

In further accordance with the present invention, the surface layer must be substantially free of spaces with a predetermined bridging distance. The bridging distance is again the dimension of the space measuring the smallest diametric distance in a direction parallel to the exterior surface. The predetermined bridging distance to be avoided is that in a range between greater than 10.0 microns and less than 1,000 microns. When the exterior surface of the surface layer has spaces with such bridging distances, undesirable macrophages form, and the fibroblasts fail to produce collagen that permits the attachment desired by the present invention.

In some embodiments of the present invention, the plurality of solid surface portions forms an integral structure that separates each space from each nearest space. For example, each space can be defined by fibers arranged into a textured polymer fiber fabric.

In other embodiments of the present invention, the plurality of spaces defines a continuum that separates each solid surface portion from each nearest solid surface portion. For example, each projection can be defined by a raised bead, a column, or a positively casted peak.

Preferably, the recesses have a minimum mean depth of about 1 micron, but the maximum depth is unknown, and depths of up to 150 microns are consistent with the structure of the present invention. In addition, the recesses can be interconnected beneath the exterior surface of the surface layer. In yet other embodiments of the present invention, adjacent recesses in one neighborhood can be substantially uniform in mean depth dimension to adjacent recesses in another neighborhood. In further embodiments of the present invention, adjacent recesses in one neighborhood can be of substantially different mean depth dimensions to adjacent recesses in another neighborhood.

In some embodiments of the present invention, adjacent projections are of substantially uniform height dimension, even though the height dimension can vary between remote sites on the surface.

In still other embodiments of the present invention, each discrete space can be defined by a pore or by a linear score.

In further embodiments of the present invention, each projection can be defined by a ridge.

In some embodiments of the present invention the surface layer is integral with the body, while in other embodiments the surface layer is a separate structure that is secured to the body.

The accompanying drawings, which are incorporated in and constitute a part of this specification, illustrate embodiments of the invention and, together with the description, serve to explain the principles of the invention.

BRIEF DESCRIPTION OF THE DRAWINGS

FIG. 6b illustrates an enlarged view of a portion of FIG. 6a.

DETAILED DESCRIPTION OF THE PREFERRED EMBODIMENTS

Reference now will be made in detail to the present preferred embodiments of the present invention, examples of which are illustrated in the accompanying drawings.

Figure 1:
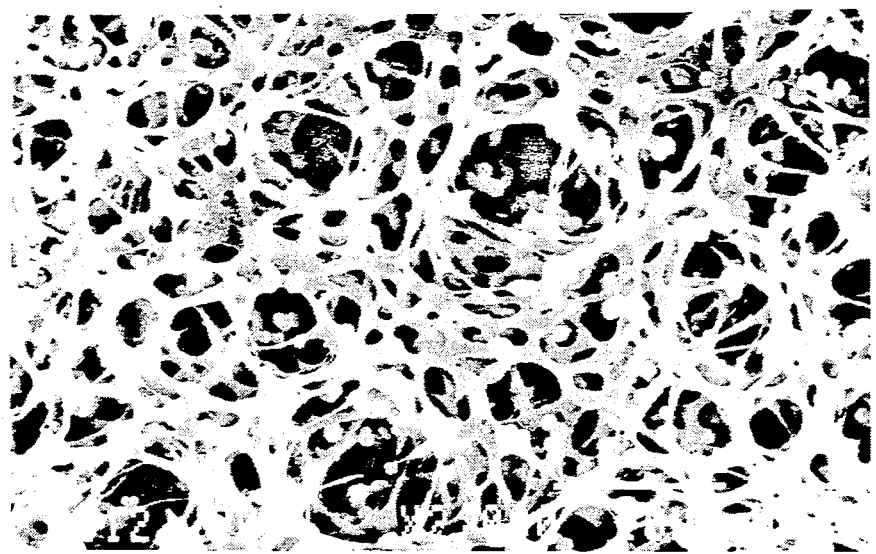
FIG. 1 is a photomicrograph magnified 2,000 times using a Scanning Electron Microscope (hereafter SEM) illustrating a surface according to the present invention, having a mean bridging distance of 1.4 microns, and with the bar in the lower right hand portion indicating the relative size of ten microns.

An example of the exterior surface topography of the micron-scale exterior surface is shown in FIG. 1 and is represented generally by the numeral 50.

As embodied and broadly described herein, an implant device structured according to the present invention is intended to be at least partially embedded at an implantation site in organic tissue of a living organism while promoting anchorage of the device at the implantation site and the growth of collagen at the implantation site, without causing encapsulation of the embedded portion of the device and without causing inflammatory tissue to form at the implantation site. Accordingly, a device structured in accordance with the present invention comprises an implant device such as the catheter for a pacemaker or for attaching a kidney dialysis machine, heart valves, vascular grafts, and plastic and reconstructive surgical materials.

Figure 2:
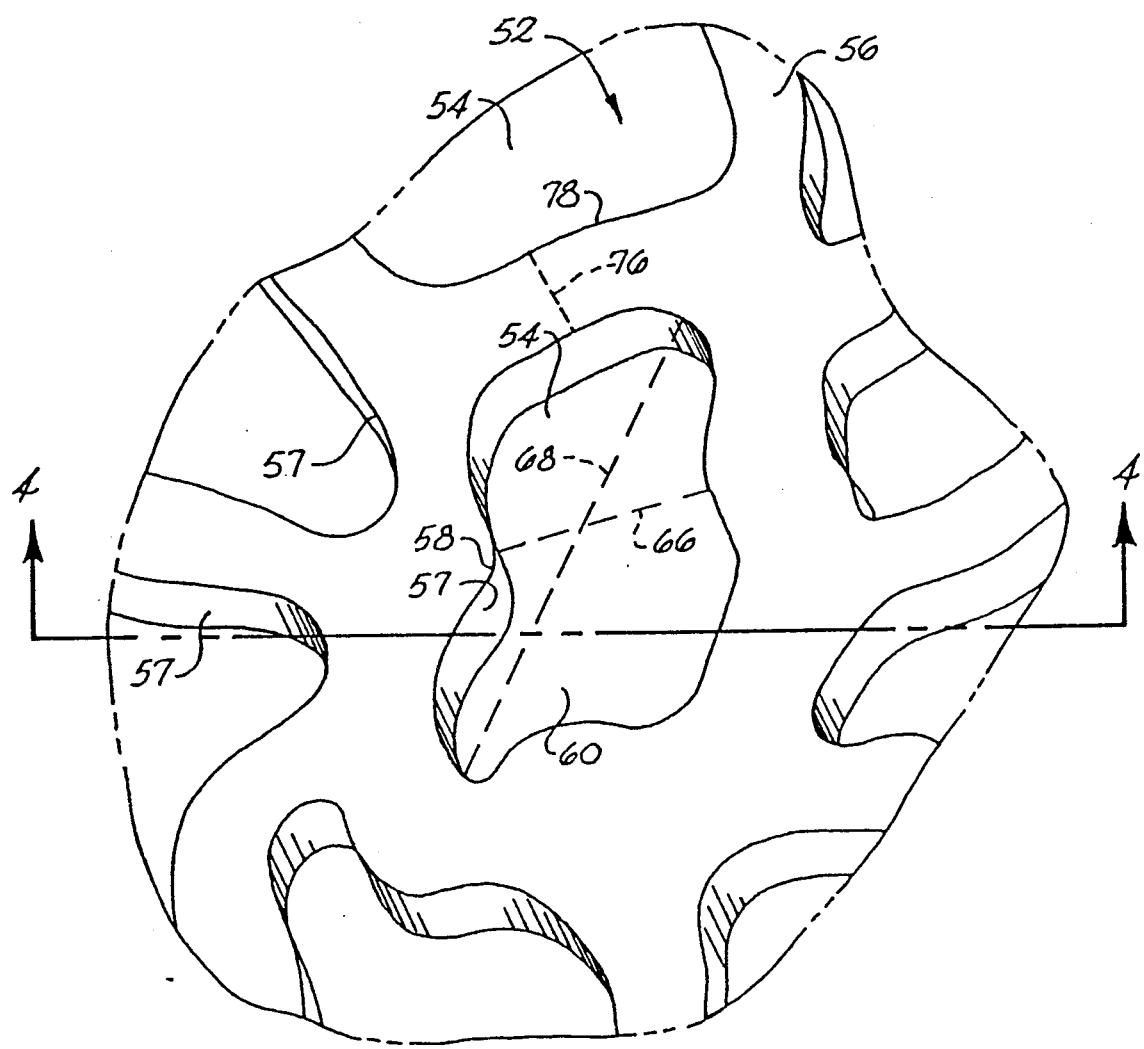
FIG. 2 schematically illustrates an elevated perspective view of a portion of an embodiment of an exterior surface of an implant in accordance with the present invention.
Figure 3:
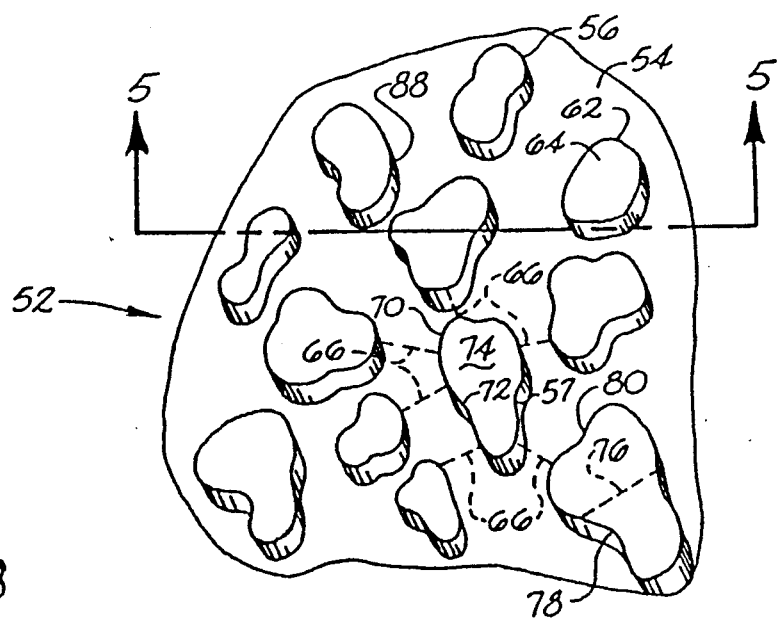
FIG. 3 schematically illustrates an elevated perspective view of a portion of an embodiment of an exterior surface of an implant in accordance with the present invention.
Figure 4:
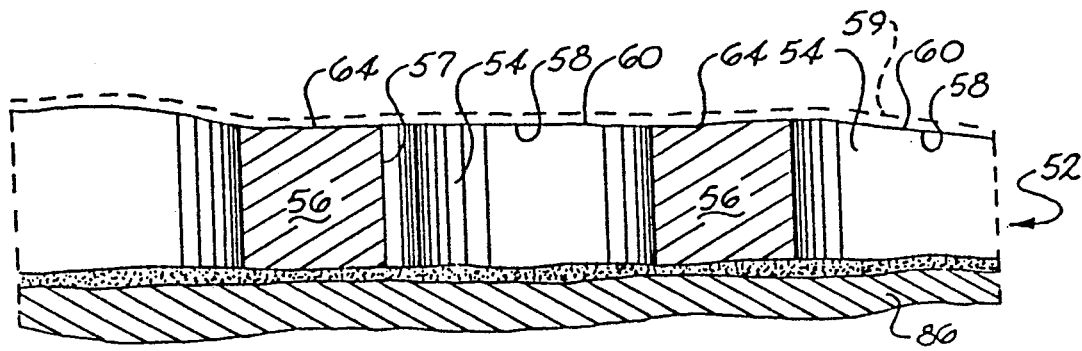
FIG. 4 schematically illustrates a cross-section view taken along the lines 4—4 of FIG. 2.
Figure 5:
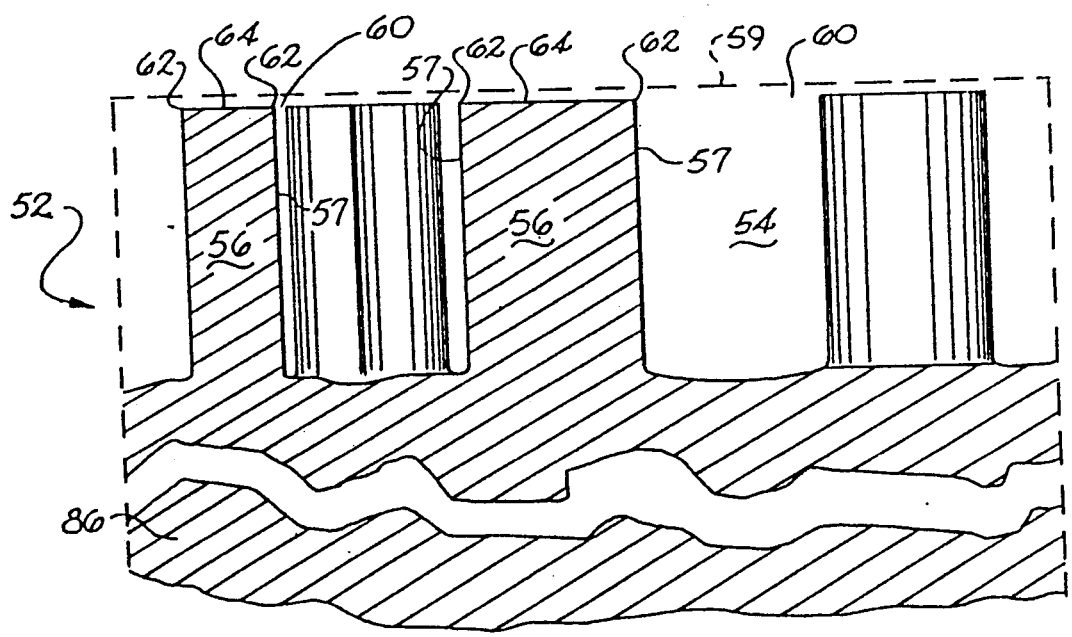
FIG. 5 schematically illustrates a cross-section view taken along the lines 5—5 of FIG. 3.
Figure 6A:
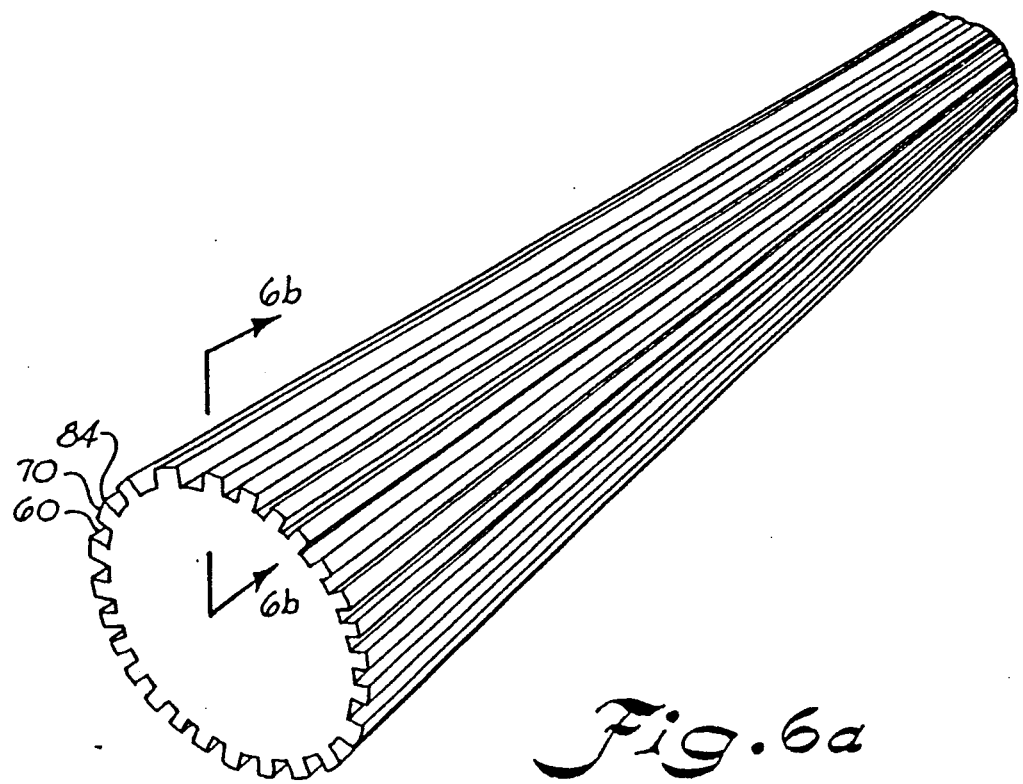
FIG. 6a illustrates a perspective view of an alternative embodiment of the present invention defining a suture.
Figure 6B:
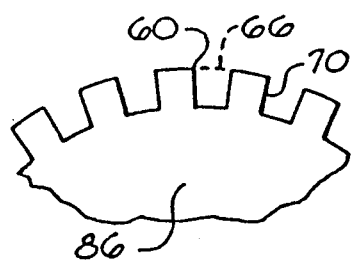

As shown for example in FIGS. 4, 5 and 6b, an implant device constructed in accordance with the present invention has a body 86 that defines a surface layer 52. The surface layer should extend over a sufficient portion of the body so that only the exterior surface of the surface layer comes into contact with the organic tissue at the implantation site. As shown in FIGS. 2 and 3 for example, a portion of a surface layer constructed in accordance with the present invention is illustrated schematically and designated generally by the numeral 52.

In further accordance with the present invention, the surface layer defines a three-dimensional pattern. As embodied herein and shown for example in FIGS. 2, 3, 4 and 5, surface layer 52 defines a plurality of three dimensional features, including a plurality of recesses 54 and a plurality of projections 56. As shown for example in FIGS. 2-5, each projection has a side wall 57 that defines at least a portion of at least one adjacent recess 54, and the recesses and projections are interspersed among each other.

In still further accordance with the present invention, each feature defines a local exterior surface for presenting itself to living cells in organic tissue adjacent the exterior surface at the implantation site. A dotted line designated 59 in FIGS. 4 and 5 defines the contour of the local exterior surface. Dotted line 59 is raised above and parallel to the local exterior surface for purposes of illustrating the contour of the local exterior surface and demonstrating that the local exterior surface encompasses and includes a plurality of spaces 60, and a plurality of solid surface portions 64. As embodied herein and shown for example in FIGS. 2-5, the exterior surface defines a plurality of spaces 60 which present themselves to the living cells and a plurality of solid surface portions 64 which present themselves to living cells.

In some embodiments, such as shown in FIG. 2 for example, a closed perimeter 58 defines each space 60 in the exterior surface of surface layer 52. Closed perimeter 58 defines the boundary of the opening to the underlying recess 54. As shown for example in FIGS. 4 and 5, each space 60 defines the exterior surface of each underlying recess 54.

In other embodiments, such as shown in FIG. 3 for example, a closed perimeter 62 defines a solid surface portion 64 therewithin. Solid surface portion 64 defines the exterior surface of each projection 56. Closed perimeter 62 forms the boundary between solid surface portion 64 and spaces 60 which form the remainder of the exterior surface of surface layer 52.

In accordance with the present invention, the smallest dimension of the spaces, not the largest, is a limiting factor concerning ingrowth or attachment of cells or cellular products. Accordingly, a bridging distance defines the minimum distance an adjacent cell must stretch to span diametrically across the spaces forming the exterior surface of the surface layer. The bridging distance is measured in a direction parallel to the exterior surface at the space in question. For example, a discrete space having an oval or ellipsoidal perimeter defines a major axis and a minor axis, and the minor axis is the bridging distance. As embodied herein and shown for example in FIG. 2, a space 60 is defined by closed perimeter 58 which forms the opening to recess 54. A dotted line 66 defines the actual bridging distance of space 60 as the minimum distance an adjacent cell must stretch to span diametrically across space 60 when measured in a direction parallel to the exterior surface at space 60. Note that bridging distance 66 differs from the distance spanned by a dotted line designated 68, which defines the major axis of space 60.

To be precise, the diametric distance is a line drawn from one side of the perimeter of space 60 to the other side of perimeter 58 of space 60 that also passes through the center of the area bounded by closed perimeter 58. However, because the mean bridging distance constitutes the significant measurement for purposes of the present invention and the number of diametric distances used to calculate the mean will be very large, a sight judgment is believed to be adequate for purposes of selecting the bridging distance across any space in the surface of implants having surface layers according to the present invention. However, the sight measurement uses a microscope to magnify the actual naked eye observation, and a minimum of 80 times magnification should be used when making the measurements in question.

For reasons explained more fully below, the mean bridging distance of the plurality of spaces in the exterior surface of the surface layer of implants according to the present invention must fall within the range of from greater than 1.0 micron to less than 4.0 microns. Preferably, the range of mean bridging distances should fall within the range of from greater than 1.4 microns to less than 1.9 microns. Thus, the odd space could have a bridging distance that measures less than 1.0 micron or more than 4.0 microns so long as the mean bridging distance of all of the spaces stays within the 1.0 micron to range.

In another alternative embodiment of the present invention, a surface layer pattern defines a plurality of discrete projections. Each of the projections extends in a direction normal to the body. The bridging distance is defined as the smallest distance separating the perimeters of the solid surface portions of adjacent projections measured in a direction parallel to the exterior surface portions. For example, for any given projection, the distance separating its exterior surface perimeter from every adjacent projection's exterior surface perimeter measured in a direction parallel to the exterior surface is determined, and these distances are the characteristic bridging distances of that particular projection.

As shown by way of specific example in FIGS. 3 and 5, recesses 54 define a continuum that surrounds projections 56. In determining the mean bridging distance of such embodiments, each projection, such as projection 70 in FIG. 3, defines a plurality of bridging distances according to the number of adjacent projections. As shown in FIG. 3 for example, each bridging distance 66 is indicated by a dotted line spanning between closed perimeter 72 of solid exterior surface portion 74 at the point closest to the closed perimeter of each adjacent projection. Again, the bridging distance is measured in a direction parallel to the exterior surface.

As explained hereinafter more fully below, the mean bridging distance of the plurality of spaces in the exterior surface of the surface layer of implants according to the present invention must fall within the range of from greater than 1.0 micron to less than 4.0 microns. Preferably, the range of mean bridging distances should fall within the range of from greater than 1.4 microns to less than 1.9 microns. Thus, the odd solid surface portion of a projection could form the boundary of a bridging distance that measures less than 1.0 micron or more than 4.0 microns so long as the mean of all of the bridging distances bounded by the plurality of solid surface portions of the projections stays within the 1.0 micron to 4.0 micron range.

Furthermore, each projection also has a breadth dimension that is defined as the smallest diametric distance of the exterior surface portion of the projection measured in a direction parallel to the exterior surface portion. In an embodiment such as shown in FIG. 2, the projection breadth dimension is measured for example as the distance indicated by dotted line 76. While in an embodiment such as shown in FIG. 3 for example, the projection breadth of a projection 78 is a line 76 spanning across a closed perimeter 80 and including the center of the area defined by closed perimeter 80. The mean breadth of the projections preferably ranges between 0.1 microns and 2.0 microns. Again, because of the large number of measurements involved, a sight selection of the breadth measurement is adequate for purposes of the present invention. However, the sight measurement is made upon magnification of the actual naked eye observation by a microscope, and the magnification should be a minimum of 80 times magnification when making the measurements in question. Again, the odd projection could have a breadth less than 0.1 microns or greater than 2.0 microns so long as the plurality of projections has a mean breadth within the 0.1 micron to 2.0 micron range.

In further accordance with the present invention, the surface layer must be substantially free of spaces with a predetermined bridging distance. These spaces to be avoided are also referred to as indentations. The bridging distance is again the dimension of the indentation measuring the smallest distance to be spanned by an adjacent cell in a direction parallel to the body. The predetermined bridging distance to be avoided is that in a range between 10.0 microns and 1,000 microns. When the surface layer has indentations with such bridging distances, undesirable macrophages form, and the fibroblasts fail to produce collagen that permits the attachment desired by the present invention.

Figure 7:
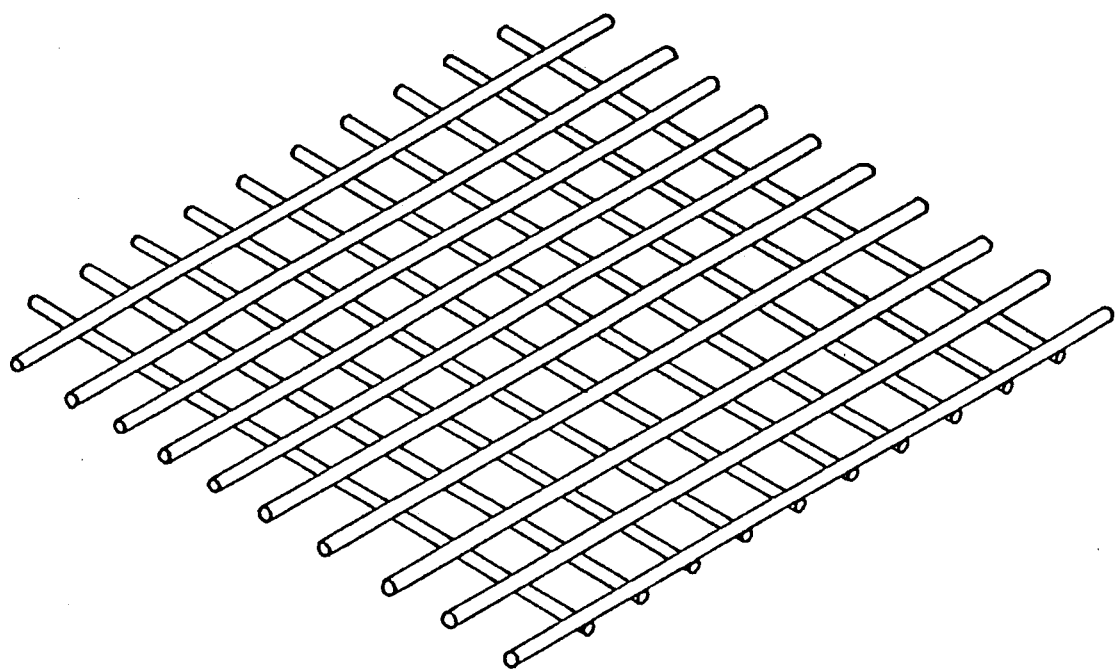
FIG. 7 illustrates a perspective view of an alternative embodiment of the present invention in the form of a textile made from randomly oriented fibers.
Figure 12:
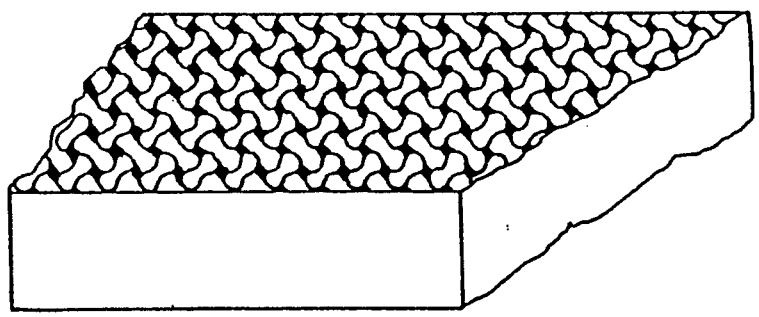
FIG. 12 illustrates a perspective view of an alternative embodiment of a surface according to the present invention in which the projections define a continuum.
Figure 13:
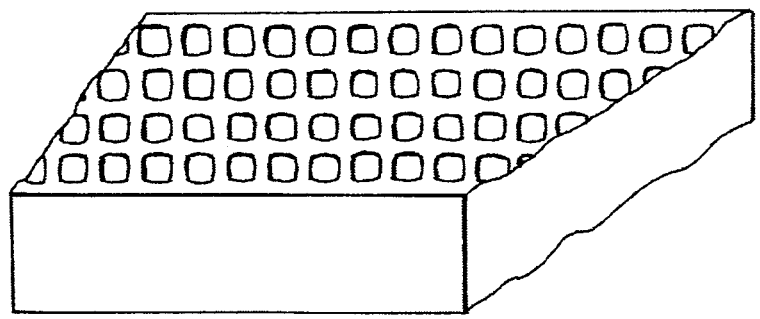
FIG. 13 illustrates a perspective view of an alternative embodiment of a surface according to the present invention in which the projections define a continuum.

In some embodiments of the present invention, the plurality of projections forms an integral structure that separates each recess from each nearest recess. As shown for example in FIG. 7, each space can be defined by fibers arranged into a textured polymer fiber fabric. The arrangement can be one in which the fibers are randomly laid and fused to one another such as by a heat treatment, as well as one in which fibers are woven together. FIG. 12 illustrates a weave pattern, and FIG. 13 illustrates a waffle pattern of projections forming an integral structure separating each opening from each nearest opening.

Figure 8:
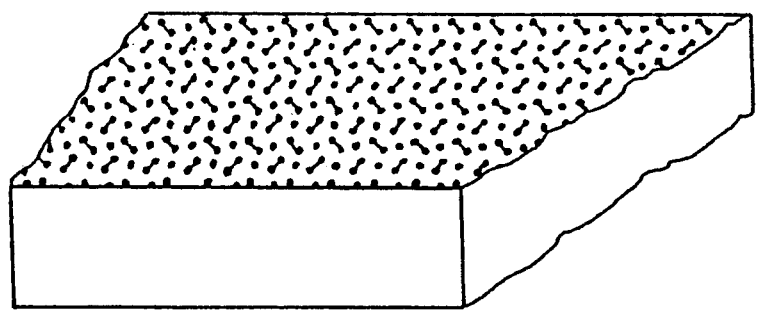
FIG. 8 illustrates a perspective view of an alternative embodiment of a surface according to the present invention in which the spaces form a continuum.
Figure 9:
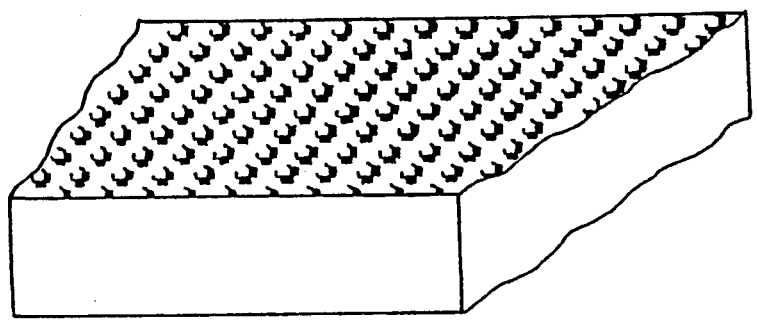
FIG. 9 illustrates a perspective view of an alternative embodiment of a surface according to the present invention in which the spaces form a continuum.
Figure 10:
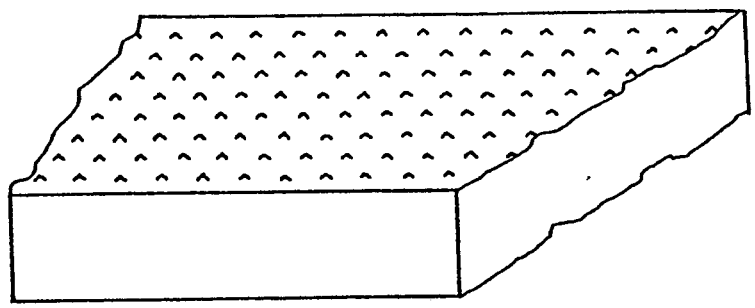
FIG. 10 illustrates a perspective view of an alternative embodiment of a surface according to the present invention in which the spaces form a continuum.

In other embodiments of the present invention such as those shown in FIGS. 8–10, the plurality of spaces are integral with one another and define a continuum that separates each discrete solid surface portion from each nearest solid surface portion. For example, each projection can be defined by a raised bead (FIG. 9), a column (not shown), or a positively casted peak (FIG. 10).

Preferably, the recesses have a minimum mean depth of about 1 micron, but the maximum depth is unknown, and depths of up to 150 microns are consistent with the structure of the present invention. In addition, the recesses can be interconnected beneath the surface layer. In yet other embodiments of the present invention, adjacent recesses can be of substantially uniform mean depth dimension. In still other embodiments of the present invention, adjacent recesses can be substantially uniform in mean width dimension. In other embodiments, the width dimensions of a single recess can vary from larger to smaller from top to bottom (FIG. 10), or vice versa.

In some embodiments of the present invention, adjacent projections are of substantially uniform height dimension, even though the height dimension can vary between remote sites on the surface.

Figure 11:
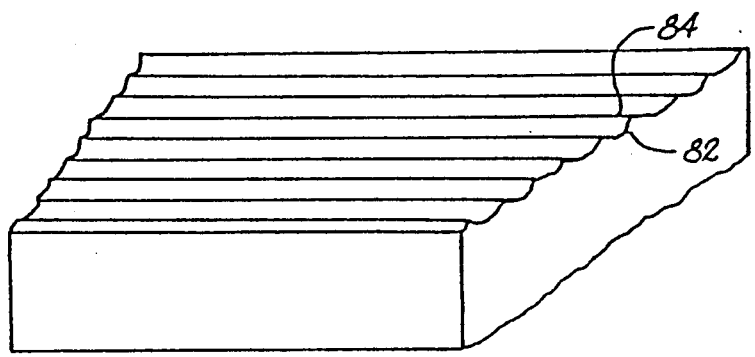
FIG. 11 illustrates a perspective view of an alternative embodiment of a surface according to the present invention.

In still other embodiments of the present invention, each space can be defined by a pore (FIG. 1) or by a linear score (FIG. 11). In yet other embodiments of the present invention such as shown for example in FIGS. 6a and 11, neither the spaces nor the projections define a continuum over the entire surface, but both describe local continuums. As shown for example in FIGS. 6a and 11, each projection can be defined by a ridge 84.

In yet further embodiments of the present invention, the spaces and solid surface portions can alternate over the exterior surface layer of a fiber intended to serve as a suture. As embodied herein and shown in FIGS. 6a and 6b for example, spaces 60 are the openings of linear grooves which alternate with solid surface portions 70. As shown in dotted line in FIG. 6b, bridging distance 66 defines the width of each opening of each groove. Such sutures can be formed by extruding same through an appropriately configured spinneret.

Current technology allows microtexturing with the use of micro-machined spinnerets. Fibers are blow spun to have grooves or ridges like the inside of a rifle barrel. Current fibers with grooves 8.0 microns wide are presently being tested in animals. New spinnerets with the appropriate dimensions of 1.0 to 2.0 microns are being manufactured by Frankl & Thomas, Inc., in Greenville, S.C. Microtextured polymer fibers will then be tested as single fibers in suture form.

In still other embodiments of the present invention, the surface layer can be made integral with the body or can be secured to the body. In the suture embodiment illustrated in FIGS. 6a and 6b for example, the surface layer is shown integral with body 86. FIGS. 1–5 illustrate surface layers which are not integral with a body but can be secured to a body 86.

HOW TO BUILD THE SURFACE LAYERS

A preferred method for configuring surface layers to be used in the present invention now is described. Positive photoresist (PR) is spin coated onto a chrome plated glass plate which has a highly controlled surface flatness. The degree of flatness must be such that a hill and valley contour of less than 10.0 microns between the highest and lowest points and less than 2 hills per glass plate are present. A pattern generator, which consists of CAD software and a personal computer, is used to produce a desired image. The generated image is sent to a light source which sends a beam of light through a lens system (similar to a microscope) onto the coated plate. Thus, the theoretical limit of accurate pattern generation is the wavelength of light used to expose the PR, and this limit is approximately 0.5 micron. The computer then controls the movement of the plate to very precisely expose the PR. The exposed PR is now etched down to the chrome. The exposed chrome is now etched with a chrome etchant down to the glass substrate. The unexposed PR is removed so that a "master" copy has been produced. Working copies are now produced by contact printing onto chrome plated glass slides. This again gives a lower limit on resolution of more or less 0.5 micron. If necessary, a step and repeat device, which also reduces the image size, can be used to reproduce the image over the entire area of a chrome plated silicon wafer. Etching of the exposed chrome leaves the final image on the wafer, which is baked and hardened at a variety of temperatures depending on the desired results. Photoresist is the dominant material involved. Silicon dioxide is not grown onto the wafer, and the silicon wafer is not etched. The images produced are not V-shaped but are straight walled. The baked PR surface is the template for surface texturing. A polymer can now be cast onto the surface to produce a negative image of the surface.

CAD allows any pattern to be generated. The only limitation is the imagination of the user. PR comes in both positive and negative forms. Thus, by coating the wafers with the proper PR, an exact or opposite image of the pattern can be obtained after polymerization.

The thickness of the PR is dependent on both spin time and speed. Lower times and speeds produce thicker coatings. Successive layers of PR can be deposited to build up to any desired thickness. Similarly the depth of etching can be controlled by exposure time and intensity of the incident light.

However, when using this method, the surface texturing of polymers is limited to materials which are semifluid and cure or harden with time. It is further currently limited to flat polymer film that will have to be attached to the implant to form its outermost surface.

REASONS BEHIND PRESENT INVENTION

Underlying the present invention is the theory of the applicants that, broadly stated, cells of living tissue respond mechanically to foreign bodies. For example, applicants' studies, the results of which are discussed hereinafter, indicate that fibroblasts appear to avoid a smooth surface much like a person walking in a stream treads lightly over slippery rocks. Moreover, when the fibroblast encounters irregularities on the order of its own size or larger, it avoids attachment to such surfaces. However, when the fibroblast encounters irregularities in a foreign body on an order of magnitude less than its own body size, it probes them with a portion of its cell mass and begins filling them with collagen by directing the flow of collagen into the recessed portions of the irregularities in the foreign body, while enveloping the protruding portions of the irregularities in the foreign body.

Applicants' research indicates that certain environmental mechanical stresses appear to be required for the formation of connective tissue. In the absence of such stresses, connective tissue is not formed or resolved, and macrophages settle in. It appears that a porous implant, such as a textile formed of fibers, having surface openings with bridging distances larger than 10 microns and smaller than 100 microns, may have macrophage accumulation in the recesses lying beneath the surface openings, even if the individual textile fibers have the approximate surface roughness of the present invention. This might further mean that vascular grafts will need to have a redesigned structure. If the graft structure is porous, it will attract macrophages; if it is non-porous (a relatively smooth continuous surface), it will lack the mechanical properties that are desired to stimulate the formation and attachment of connective tissue.

Applicants further conclude that fibroblasts that avoid attachment to an implant surface invite the presence of or tolerate the presence of leukocytes, specifically macrophages, to fill the space between the fibroblasts and the implant's surface. The mechanism triggering formation of the macrophages could be one of the following two possibilities:

(1) fibroblasts that are not securely anchored in space produce imperfect extracellular material, which forms an extracellular matrix that attracts macrophages;

(2) fibroblasts may not tolerate shear stresses from motion against a material's surface, and thus such shear stresses would lead to cell injury and death. This is consistent with the fact that fibroblasts lack surface cell layer properties that would otherwise protect them from shear stress injuries. This may continuously happen with approaching fibroblasts. The resultant cell morbidity/mortality may attract macrophages. Once the macrophage population exists, it persists because the original problem also persists.

Applicants' findings also appear to indicate that fibroblasts attaching to a suitable surface, such as that employed by the present invention, transform into fibrocytes and are surrounded by their extracellular matrix product. Macrophages are to a large extent absent.

Applicants have measured collagen that reaches into voids of the implant surface for lengths of up to 150 microns.

TEST OBJECTIVES

Tests were performed to establish the optimum size of the surface openings for the surface layer of the present invention. The tissue response to tested implants was compared by keeping the surface geometry constant. Implants with hydrophilic materials forming the surfaces exposed to tissue were compared to implants with hydrophobic materials forming their surfaces. In addition, the surface geometry was varied in each of the hydrophilic and hydrophobic materials to compare the effect of surface geometry. All of the tests involved the implantation of the selected materials subcutaneously in the dorsum of mongrel dogs. All of the hydrophilic implants were studied at two and twelve weeks, while the hydrophobic implants were studied at two weeks only.

The two-week and twelve-week evaluation periods were selected because at two weeks the acute inflammatory reaction has ended, but changes are still taking place in the implant capsule. At twelve weeks, the response is expected to be in a stabilized condition at the implant/tissue interface.

TEST IMPLANTS

One material suitable for use as the test implants for the surface of embodiments of the present invention is sold under the name VERSAPOR and is available from Gelman Sciences of Ann Arbor, Mich. VERSAPOR is a polymeric filter material composed of a porous coating of a polyvinyl chloride/polyacrylonitrile (PVC/PAN) copolymer over a non-woven mesh of nylon fibers. The nylon fibers have a mean diameter of 25 microns. The nylon mesh is dip-coated in a resin of the copolymer and solvents. The pore size is controlled primarily by varying the composition of the copolymer resin mixture. The filter then undergoes gelation lying flat while being exposed to a series of "environmental chambers."

All of the tests were conducted using the VERSAPOR material. The silicone-coated VERSAPOR material test implants are identified as hydrophobic (H), and the test implant materials without the silicone coating are identified as hydrophilic. The hydrophobic variety is made by dipping the hydrophilic material into a solution of a silicone compound of approximately ten percent concentration.

VERSAPOR is manufactured with five different nominal pore sizes from 0.2 to 10 microns in diameter. All five of the available pore size materials have the same chemical composition, which is also available both with and without a thin coating of silicone. The silicone coating does not affect the pore size. Gelman identifies its VERSAPOR materials according to the pore size and whether it is hydrophilic or hydrophobic, an H indicating hydrophobic. For example, a Gelman identification of V-200 corresponds to a rated pore size of 0.2 microns and a hydrophilic material. Similarly, a Gelman identification of V-3000H corresponds to a rated pore size of 3.0 microns in the hydrophobic embodiment. Other rated pore sizes for the hydrophilic material include 1.2 microns (V-1200), 3.0 microns (V-3000), 5.0 microns (V-5000) and 10.0 microns (V-10,000), while the other rated pore sizes for the hydrophobic materials include 0.2 microns (V-200H), 1.2 microns (V-1200H), and 5.0 microns (V-5000H).

The brittleness and lack of mechanical strength probably makes the PVC/PAN copolymer material used in the VERSAPOR materials unsuitable for a soft tissue implant in commercial use. However, the availability of this filter material with differently sized openings made it ideal for use as a test model for studying the effects of variation in mean bridging distances.

PREPARATION OF TEST IMPLANTS

Sheets of each of the VERSAPOR test materials were cut into samples measuring 1.0 centimeter by 2.0 centimeters. The materials were subjected to an implant cleaning procedure consisting of ultrasonic cleansing and sterilization using ethylene oxide according to standard procedures.

In general, the test materials were white, opaque sheets resembling bond paper. It appeared that the copolymer in the tested samples contained more PVC than PAN. In most cases the presence of the underlying nylon fibers was apparent to the naked eye, giving it a slightly rough texture. The surface porosity was too small to be seen with the naked eye, and even with standard reflected light microscopy appeared only as a grainy texture on the surface.

TABLE I

THICKNESS OF VERSAPOR MATERIALS

| Material | Means (μm) | Standard Deviation (μm) |
| --- | --- | --- |
| V-200 | 221 | 9.14 (4.14%) |
| V-1200 | 237 | 14.5 (6.12%) |
| V-3000 | 220 | 12.6 (5.73%) |
| V-5000 | 171 | 12.6 (7.39%) |
| V-10,000 | 170 | 11.8 (6.96%) |
| V-200H | 181 | 10.3 (5.70%) |
| V-1200H | 245 | 15.5 (6.31%) |
| V-3000H | 228 | 20.9 (9.17%) |
| V-5000H | 167 | 14.1 (8.44%) |

The implant materials presented three slightly different topographies, apart from the differences in pore size. When viewed with the SEM, the V-200, V-200H, and V-1200H appeared as interconnecting holes in a matrix of material. The other VERSAPOR materials, V-1200, V-3000, V-3000H, V-5000, V-5000H, appeared as a fine mesh of interconnecting spicules. The coating on the V-10,000 material appeared as irregular clusters of globules.

The V-1200 material had the appearance of white paper, the surface was uniform, and the underlying fibers were clearly defined. Under the microscope, both sides presented a uniform grainy white surface, with the underlying nylon fiber network visible as shadows underneath, and some fibers appearing close to the surface. As shown in FIG. 1, examined at a magnification 2,000 times actual size with a scanning electron microscope, the copolymer coating of the V-1200 material appeared as a reticular mesh of interconnecting tortuous spicules. The mesh formed irregularly shaped interconnecting voids of varying size. The V-1200 material had more void space than material. The surface was uniform and was the same on both sides. No underlying fibers were visible using the SEM. One of the micrographs revealed a crack in the coating and this taken as a warning that the fragility of these materials raises the possibility that minor damage to an implant can cause voids much larger than the mean bridging distance. The V-1200H material (not shown), appeared to have more material than the V-1200, with broader spicules separating the recesses and almost no globules of material.

Additional samples of each differently sized material were prepared for examination by scanning electron microscope. Micrographs were taken at magnifications ranging from 150 to 6,000 times. These micrographs were used to analyze the sizes of the surface openings. The pore size stated by the manufacturer of the VERSAPOR material refers to the size of the particles that can pass through it, since the material is intended for use as a filter. However, these rated pore sizes do not necessarily indicate the size of the openings on the surface of the filter, and it is these surface opening sizes that are important for the purposes of the present invention.

Thus, these surface opening sizes were determined experimentally as follows.

MEASURING SIZE OF MEAN BRIDGING DISTANCES ACROSS SURFACE OPENING

Scanning electron micrographs were taken at four randomly selected locations on each material at magnifications selected to show fair representations of the surface topography. For example, a small opening size required high magnification, while a larger opening size required commensurately lower magnification. A micron mark in the form of a white bar was labeled 1.0 micron, 10.0 microns, etc., and was present in each photograph to enable accurate scale identification. The micrographs were enlarged to 8 by 10 inch prints to make the measurement process easier. A computerized image analysis system connected to a video camera was used to measure the sizes of the surface openings and the surface densities of the openings. This system was capable of displaying, recording, and storing measurements of various parameters and performing statistical analyses on recorded data. Interaction with the system includes use of a puck appearing on a digitizing pad. The position of the puck on the pad was displayed as cross-hairs on a video display terminal, and in the data acquisition mode the puck was used to mark distances, trace objects, and make all entries.

A square sample selected to contain an estimated 40 to 60 openings was framed on each micrograph. An image of this square sample was displayed on the video display terminal. The puck traced the periphery of each opening in the sample area, and the short diameter of each opening was chosen by eye, traced and entered as the bridging distance data. The software package of the system was used to compute mean bridging distance, standard deviation, and standard error for each of the materials measured. The surface opening density was calculated for each material by counting the total number of openings and dividing by the total area of the square sample area.

Because of the character of the materials, deciding what to call a surface opening was often difficult, and personal judgement was involved. There was high variability in the opening size measurements for all of the materials. However, the measurement of a large number of openings for each material offered statistical significance to the results.

The mean bridging distances of the V-1200 and V-3000 materials were very close, namely, 1.42 microns and 1.83 microns, respectively. The hydrophobic counterparts of these two materials, V-1200H and V-3000H, had no significant difference in mean bridging distance, namely, 1.88 microns and 1.87 microns, respectively.

The mean bridging distances across the surface openings and the standard deviations for each of the eight materials measured are listed in Table II.

TABLE II

BRIDGING DISTANCES OF VERSAPOR MATERIALS

| Material | Rated Pore Diameter (μm) | Mean Bridging Distance (μm) | Standard Deviation (μm) | N |
| --- | --- | --- | --- | --- |
| V-200 | 0.20 | 0.42 | 0.22 | 203 |
| V-1200 | 1.20 | 1.42 | 0.92 | 243 |
| V-3000 | 3.00 | 1.83 | 0.88 | 171 |
| V-5000 | 5.00 | 3.33 | 1.55 | 193 |
| V-10,000* | 10.00 | 3 to 14 | — | 18 |
| V-200H | 0.20 | 0.48 | 0.22 | 160 |
| V-1200H | 1.20 | 1.88 | 0.85 | 213 |
| V-3000H | 3.00 | 1.87 | 0.93 | 188 |

TABLE II-continued

| BRIDGING DISTANCES OF VERSAPOR MATERIALS | | | |
|---|---|---|---|
| Material | Rated Pore Diameter (μm) | Mean Bridging Distance (μm) | Standard Deviation (μm) | N |
| V-5000H | 5.00 | 3.61 | 1.42 | 233 |

N is the number of measurements.
*V-10,000 was not measured using the standard procedure described above. Instead, one 1,000 times magnification micrograph was taken and used to measure the transverse width of the large irregular voids and valleys.

The results of the surface opening density calculations are tabulated in Table III.

TABLE III

| CALCULATED SURFACE OPENING DENSITIES FOR VERSAPOR MATERIALS | |
|---|---|
| Material | Surface Opening Density (Openings/mm$^2$)($\times 10^3$) |
| V-200 | 793 |
| V-1200 | 97.2 |
| V-3000 | 47.5 |
| V-5000 | 19.3 |
| V-10,000 | N/A |
| V-200H | 625 |
| V-1200H | 59.2 |
| V-3000H | 52.2 |
| V-5000H | 16.2 |

IMPLANTATION OF THE TEST IMPLANTS

After the subcutaneous implants tested were ultrasonically cleaned and sterilized using ethylene oxide according to standard procedures, they were placed subcutaneously in the dorsum of mongrel dogs using general anesthesia and standard surgical procedures. At the conclusion of the selected implant residence period (either two weeks or twelve weeks), the animals were sacrificed and the implants, with surrounding tissue, were dissected out and placed in formalin.

Three dogs were used for the two-week implant study. One implant of each of the nine test materials plus a second V-10,000 implant (to check for symmetry of healing was implanted in each dog.

Four dogs were used for the twelve-week implant study. Two of these dogs received two V-1200 implants. Each of the other dogs received two implants of each of the following: V-200, V-3000, V-5000, and V-10,000. The hydrophobic materials were not tested in the twelve week study.

EXAMINATION OF THE EXTRACTED TEST IMPLANTS

The formalin-fixed tissue specimens were trimmed to remove any extraneous tissue and embedded in paraffin according to standard dehydration and embedding techniques. The specimens were sectioned at 5.0 to 7.0 microns and seven slides were made from each. Two slides from each specimen were stained with hematoxlyn and eosin (H&E) for general evaluation of tissue morphology and cellularity, and two slides were stained using Masson's trichrome method for collagen, which differentiates collagen by staining it blue. The procedures for all stains used can be found in *Manual of Histological Staining Methods*. Luna, L. G. ed., McGraw-Hill, N.Y., 1960, 3rd ed. After evaluation of the H&E and trichrome stained slides, sometimes additional stains were used. The Brown and Brenn method was used to stain specimens for bacteria. The Gomori method was used to stain specimens for reticulum. The Turnbull Blue method was used to stain specimens for hemosiderin.

The evaluation focused on the growth of cells or extracellular material through the surface openings into the surface layer recesses, the types of cells and relative quantities of different types at the implant/tissue interface, the contact and apparent adherence of cells or connective tissue to the implant surface, the capsule thickness, and the apparent maturity of surrounding connecting tissue. These evaluations were made primarily on a qualitative basis and used to obtain a general appraisal of the implant anchorage in the surrounding tissue bed.

The following standard evaluation method was applied to each of the histological slides. The examination was conducted on a biological microscope at magnifications of between 40 and 100 times. The thickness of the implant capsule was measured and expressed either in cell layers if the capsule was very thin, or in microns. One cell thickness corresponds to approximately 10.0 to 12.0 microns. The percentage of the portion of each capsule which appeared to be adhered to the surface was estimated. The capsule was assumed to be adherent if it was observed to be making intimate contact with the implant surface. This was a good assumption, because in cases where there evidently was no adhesion, the tissue separated from the implant during harvesting or sectioning, or simply was not in contact in vivo. and a separation was visible on the sections.

The cells surrounding the implant were subjected to a qualitative analysis which included identifying the predominate cell type at the tissue/implant interface. This included acute inflammatory cells (PMN's), chronic inflammatory cells (macrophages and giant cells), fibroblasts, or fibrocytes. The relative quantities, e.g., sparse or abundant, and their location, e.g., focal or spread throughout the capsule, were also noted.

The presence of any tissue component (cells, detritus, connective tissue, capillaries) inside the implant was noted. The location of chronic inflammatory cells, if any, also was noted. The various locations identified included on the surface, in surface openings or on bumps, inside the implant, or in defects in the coating. Other notable observations that were recorded included, the presence of free red blood cells, infection, parasites, etc. The presence or absence of collagen in contact with the implant was noted, and if any such contact existed, the amount and nature were also noted. The maturity of collagen in contact with the implant was noted. The maturity judgement was based on the appearance of the collagen strands and the darkness of the Blue stain. Collagen maturity was judged on a scale of zero to three, with zero indicating none present against the implant and three indicating collagen similar in appearance to that in normal mature dermis.

GENERAL RESULTS OF EXAMINATION OF TESTED IMPLANTS

There was little or no variation among implants of the same material. All implants of one given material showed separation, while all implants of another material showed intimate contact.

Upon completion of all the individual slide evaluations noted above, implant summaries were compiled for each implant, and these summaries were used to yield complete and detailed summaries of the tissue reactions to each of the different materials for each time period. For example, one summary was generated for each surface opening size for the two-week hydrophilic implant. Another summary was generated for each surface opening size for the two-week hydrophobic implant. Yet another summary was generated for each surface opening size for the twelve-week hydrophilic implants. These summaries are presented hereinafter. An attempt was made in these studies to characterize a typical response for each material tested.

NAKED EYE INSPECTION OF TEST IMPLANTS

Upon retrieval, all of the implants had been covered by a thin, transparent film of connective tissue, and no macroscopic signs of inflammation or fluid accumulation were visible. Small blood vessels were observed lying across the surfaces of the implants, and there were no macroscopically visible differences in the tissue reactions to any of the implants, with the possible exception that the connective tissue capsules around the twelve-week implants appeared to be slightly less transparent than those around the two-week implants.

SUMMARIES

V-200 Hydrophilic Implants

Figure 14:
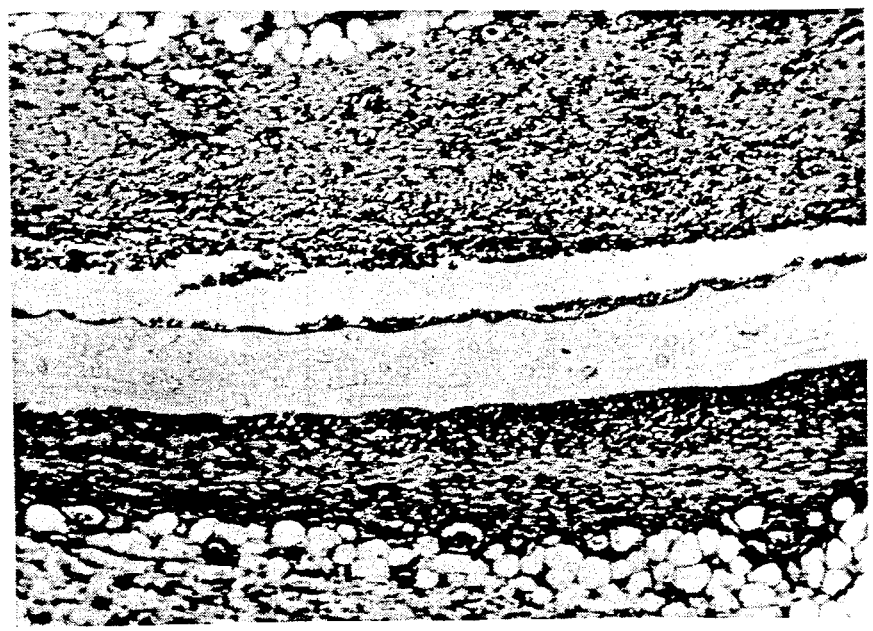
FIG. 14 illustrates (magnified 80 times) a section showing the bad result obtained when an implant has a surface in which the mean bridging distance is 0.42 microns. A mechanical separation (S) has developed within the macrophage layer (shown by the arrows) that separates the thick granulation tissue capsule (G) from the implant (V).

As shown in FIG. 14 for example, at two weeks, these implants evoked a chronic inflammatory response with a thick capsule. The capsule (G) tended to separate from the implant (V) during handling and sectioning, and this indicated that there was little tissue adhesion to the implant. There was no collagen in contact with implants. There were no cells visible inside the implants, which had a mean bridging distance of 0.42 microns.

At twelve weeks, there was still no adherence between the tissue capsules and these implants. The capsules had contracted and severely distorted and curled the implants. This distortion and curling resulted in void spaces. The reaction to these implants appeared to be very similar to the long-term response observed with smooth-surfaced biocompatible materials such as silicone or polyurethane. There were no cells, collagen, or reticular fibers apparent inside these implants.

V-200H Hydrophobic Implants

In the two-week implants, which was the only time period tested, the tissue reaction was the same as that to the hydrophilic V-200 implants, except that the tissue capsule was generally somewhat thinner (60 to 270 microns), and occasionally only several cell layers thick. There was no collagen contact with the implant.

V-1200 Hydrophilic Implants

Figure 15:
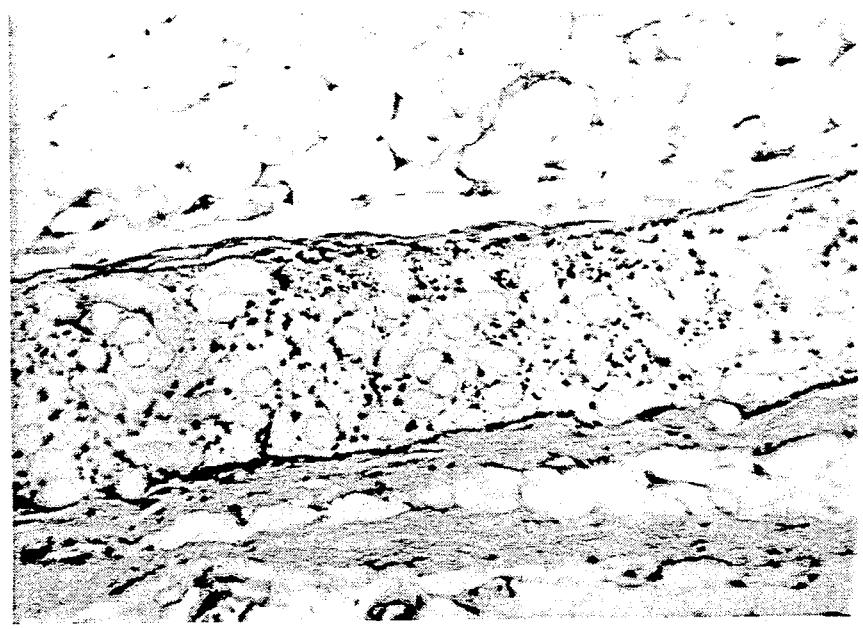
FIG. 15 is a 200 times original magnification light micrograph showing a section after two weeks of implantation with a device having a surface according to the present invention with a mean bridging distance of 1.4 microns. The arrows point to a thin fibrous capsule that lies directly along the implant surface.

The V-1200 implants had a mean bridging distance of 1.42 microns. At two-weeks, the hydrophilic V-1200 implants were encircled by a thin (1 to 5 cell thickness) and uniform, adherent fibrous capsule. As shown for example in FIG. 15, the implants were lined around most of the periphery by a single layer of fibroblasts or spindle-shaped fibrocytes. Some giant cells were observed. A few giant cells were observed along the implant surface, but most of the observed giant cells were observed to be located in cavities and around exposed nylon fibers. A few macrophages and/or fibroblasts were observed to be confined to cavities. A thin layer of collagen lay over the cell layer and made apparent direct contact with the implant surface at numerous points and over extended areas. The capsule appeared to be 100% adherent and there was no separation between capsule and implant.

Figure 16:
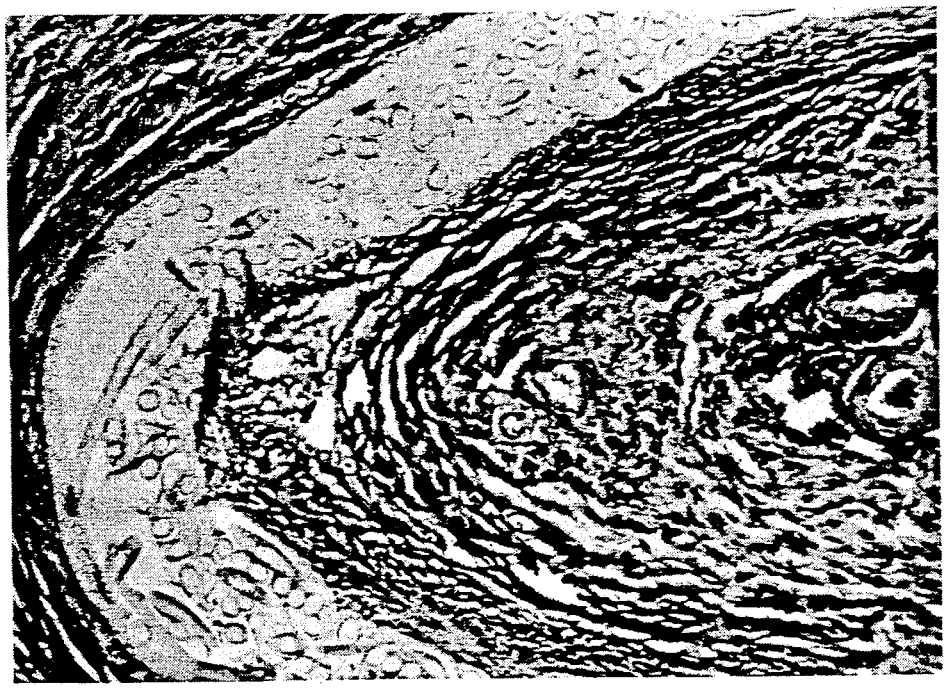
FIG. 16 is a 100 times original magnification light micrograph showing a section after twelve weeks of implantation with a device having a surface according to the present invention with a mean bridging distance of 1.4 microns. A fibrous capsule remains adherent to the implant surface, even though a section of the implant has been torn during the sectioning of the tissue sample containing the implant.

As shown in FIG. 16 for example, there were areas where the surface layer, i.e., the copolymer coating, was stuck to the collagen strands and pulled off of underlying nylon fibers, indicating a strong bond between the fibroblasts or collagen and the surface layer. Apparently, the bond between the copolymer surface layer and the underlying fibers was not as strong as the bond between the surface layer and the tissue adjacent the surface layer. There were very few capillaries and small blood vessels within the connective tissue capsule. A few red blood cells and scattered pyknotic cells appeared inside the implants.

One implant was filled with an abundance of red blood cells and interspersed white blood cells, the origin of which could not be satisfactorily explained. For example, a stain for hemosiderin was negative, and no phagocytic cells were found inside the implant. One implant also had two focal sites of inflammatory cell accumulation. In one of these sites there were large giant cells around a protruding nylon fiber, and the other site showed some small, non-stained, illuminescent particles which resembled the copolymer material.

The twelve-week implants exhibited the same thin, adherent collagen capsule seen after two weeks, although in a few cases it was slightly thicker (1 to 10 cell thicknesses). The capsule surrounding the twelve-week V-1200 implants consisted exclusively of mature collagen bundles and inactive fibrocytes, surrounded by loose connective tissue. The implant/tissue interface seemed to be perfectly stable. These long-term capsules contained very few cells in comparison to the two-week implants. No cell layer separated the collagen capsule from the implant surface, and this was one noted difference from the two-week implants. Macrophages or giant cells which may have been present along the surface earlier had disappeared by twelve-weeks, except for those in concave indentations in the surface.

Figure 17:
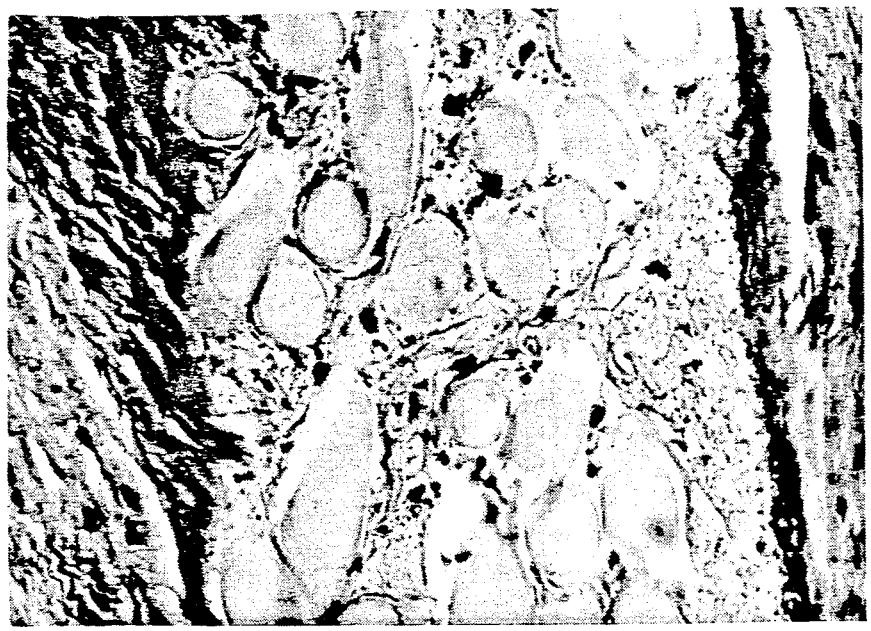
FIG. 17 is a 500 times original magnification light micrograph showing a section after twelve weeks of implantation with a device having a surface according to the present invention with a mean bridging distance of 1.4 microns. The arrows point to collagen strands which are penetrating throughout the porosity of the implant beneath the surface layer.

As shown for example in FIG. 17, the collagen was in continuous contact with the twelve-week V-1200 implant surface, and had two different appearances. Some appeared in the form of strands lying along the surface, parallel to the implant, and some appeared as brush strokes sweeping from the outer bundles toward the implant's surface. The collagen capsule seemed to be adherent over 100% of the implant surface, and the collagen/surface layer interface appeared strong. A reticulum stain prepared from one implant revealed a single, thin layer of silver-stained fibers lying directly along the entire implant surface, occupying the same region as the collagen, with apparent adherence. There were a few small blood vessels around the outer edge of the capsule, and there were occasionally capillaries or small vessels inside the capsule, lying directly against the implant. Only sparse pyknotic cells and a few macrophages and/or fibroblasts were observed inside these implants. One of the twelve-week implants became folded, and fine, pale strands of collagen penetrated inside the apex of the curve of this implant to a depth of 100 to 200 microns without accompanying cells. It is suspected that the collagen may have been able to penetrate the implant at this site through cracks in the coating caused by bending. The folded implant also showed several focal sites of chronic inflammation, without evidence of bacteria or contaminant particles.

V-1200H Hydrophobic Implants

The hydrophobic V-1200H implants had a mean bridging distance of 1.88 microns. At two weeks, these implants elicited a mild connective tissue reaction remarkably similar to the V-1200 hydrophilic implants after two weeks. The V-1200H hydrophobic implants developed a thin, adherent collagen capsule (1 to 7 cell thicknesses) with few cells. The collagen capsule was usually separated from the implant by a single layer of cells (fibroblasts) like the V-1200 capsule, but there were many more cells, forming a more continuous layer. Some fibroblasts and/or macrophages and a few giant cells were also seen along the surface. Undulations in the coating surface caused by the nylon fibers coincided with more inflammatory cells than on the V-1200 implants at two weeks. The connective tissue capsule appeared to be attached to the V-1200H surface layer along both sides of the entire implant. Collagen, however, was only seen to make contact with the V-1200H implant at several points; noticeably less than on the hydrophilic V-1200 implants.

V-3000 Hydrophilic Implants

The V-3000 implants have surface openings with a mean bridging distance of 1.83 microns.

An error in implant placement for the two-week V-3000 implants precluded the gathering of data.

However, the twelve-week implants developed capsules that were the same qualitatively as those seen around the V-1200 implants, although there was a tendency for the V-3000 implant capsules to be slightly thicker. The tissue reaction was judged to be good to excellent.

The capsules were thin to moderately thick (1 to 10 layers of collagen strands, approximately 100 microns) adherent collagen, with few cells, mostly fibrocytes. Giant cells were only observed in undulations and the larger defects on the surface and occasionally inside, and no macrophages were observed at the interface. The implant capsule was purely fibrous and the collagen made continuous contact with the implant over the entire periphery. Both "brush stroke" and "parallel" collagen forms were seen. These V-3000 implants seem to have more surface undulations than the V-1200 implants, and where these undulations occurred there were accumulations of giant cells. The collagen quality appeared moderate to very good, and the collagen bond to the coating material appeared to be stronger than the cohesive strength of the material. There were more pyknotic cells inside the V-3000 implants than in the V-1200 implants. There also were occasional giant cells, capillaries, and a few larger vessels. The larger structures such as the giant cells and vessels were seen where the surface layer was defective or non-uniform. One implant had a large chronic inflammatory site.

V-3000H Hydrophobic Implants

The V-3000H implants had surface openings with a mean bridging distance of 1.87 microns.

Figure 18:
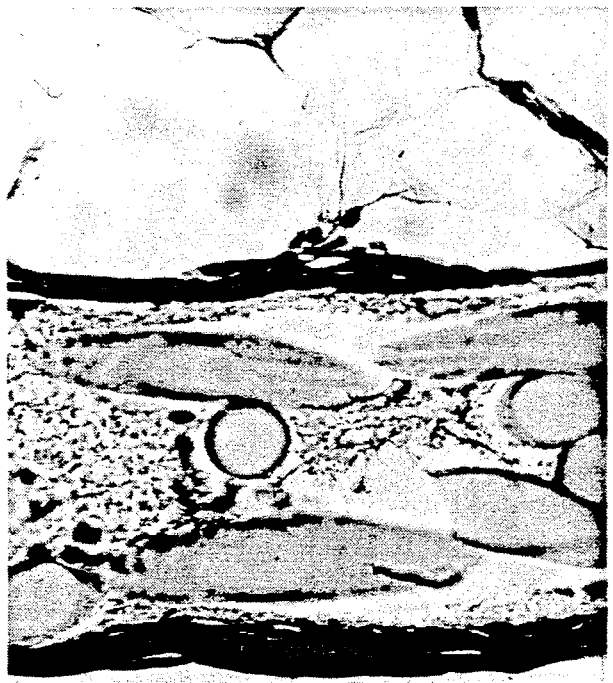
FIG. 18 is a 500 times original magnification light micrograph showing a section after two weeks of implantation with a device having a surface according to the present invention with a mean bridging distance of 1.9 microns. Collagen fibers are attached to the surface of the implant and inflammatory cells are absent from that surface.

After two-weeks, the implants had very thin, adherent capsules (1 to 6 cell thicknesses). In some areas, the tissue reaction was so mild that it was difficult to distinguish the thin implant capsule from the surrounding tissue. This material caused little or no insult to the host tissue. The response showed similarities to the V-1200 and V-1200H responses and the V-3000 twelve-week response. Like the twelve-week V-3000 implant capsules, these two-week V-3000H implant capsules contained few cells, and the cells present were mostly fibrocytes. There were some areas of macrophages and fibroblasts, and as seen with the twelve-week V-3000 implants, numerous undulations in the implant surface were filled with giant cells. As previously stated, it is believed that the presence of these inflammatory cells in the undulations is due not to the character of the surface layer, but to the larger unevenness caused by the underlying nylon fibers. As shown in FIG. 18 for example, at two weeks the implant capsule appeared to be adherent over the entire surface of the V-3000H implant. The V-3000H implants did not have the uninterrupted layer of fibrocytes separating the collagen from the implant, as did the V-1200H implants. Collagen made contact with the surface at frequent spots, and there were some long continuous areas of contact with apparent adhesion. Qualitatively the response of the V-3000H implants at two weeks was similar to the twelve-week V-3000 implants, although the collagen contact was not as extensive in the V-3000H implants.

A Gomori stain for reticulum, which is one of the products of fibroblasts, revealed a fine layer of silver-stained reticulum fibers around the implant, but this layer was usually not in contact with the implant surface. Scattered dark pyknotic cells and some oddshaped red blood cells were seen inside the V-3000H implants. No collagen was seen inside the two-week implants, nor were there any giant cells or positively identifiable capillaries, as there were in the twelve-week V-3000 implants.

V-5000 Hydrophilic Implants

The V-5000 implants had surface openings with a mean bridging distance of 3.33 microns.

Two of the two-week V-5000 implants evoked a chronic inflammatory reaction, while one developed a thin adherent collagen capsule. The fibrous tissue capsule was separated from the implant by a layer of cells and made no direct contact with the implant.

The collagen capsule around the V-5000 implant without the inflammatory reaction was thin (1 to 5 cell thicknesses) and was generally separated from the implant by a one-cell layer of fibrocytes. It made contact with the surface at frequent points. The capsule seemed to be adherent to the implant, but the collagen appeared to be of poor quality.

One implant developed a bilateral focal area of acute inflammation, and another had three separate sites of acute inflammation. This may have been caused by the presence of some small granules of an unidentified contaminating material.

After twelve-weeks, the V-5000 implants were surrounded by tightly adherent fibrous tissue capsules. Two developed thicker capsules (60 to 300 microns), and one developed a very thin capsule (3 to 4 cell thicknesses). The chronic inflammatory reaction at the implant/tissue interface observed in the response to these implants of this material at two weeks was absent at twelve weeks. Collagen fibers appeared to make continuous contact with the implant, and the collagen was mostly of the "brush stroke" type, although some "parallel" was present. Collagen was observed protruding into the recesses of the implant surface layer, and there were some fine strands throughout the implant surface layer. The collagen capsule appeared to be adherent over 100% of the implant surface, and the presence of collagen fibers protruding into the recesses implied that there was a strong bond. The collagen was of varying quality, ranging in its appearance from pale to darkly stained. There were very few small blood vessels in the capsule. Scattered pyknotic cells, macrophages, fibroblasts, capillaries, vessels, and a few red blood cells were seen inside the implant. In the areas where collagen strands were seen extending through the implant surface openings, there were no macrophages or giant cells.

V-5000H Hydrophobic Implants

The V-5000H implants had surface openings with a mean bridging distance of 3.61 microns.

At two-weeks, the V-5000H implants displayed a tissue reaction that was virtually the same as the two-week response to the hydrophilic V-5000 implants, except that the capsule was thinner. The V-5000H implants were surrounded by a thin capsule (0 to 7 cell thicknesses) of loose, newly formed connective tissue. This connective tissue capsule contained fibroblasts and some fibrocytes, but as was seen on the hydrophilic V-5000 implants, there was a layer of giant cells and macrophages separating it from the implant surface. Like the V-5000 hydrophilic implants, these V-5000H implants seemed to be anchored to the inflammatory cells. There appeared to be no contact between the collagen capsule and the V-5000H implant surface, but the surface layer was difficult to identify, and there may have been a few spots of contact.

The same undesirable elements found within the V-5000 implants were seen in the V-5000H implants. There were macrophages, giant cells, capillaries, and pyknotic cells.

V-10,000 Hydrophilic Implants

The V-10,000 implants had surface openings with a mean bridging distance of 3.0 to 14.0 microns.

At two-weeks, the histological response to the V-10,000 implants was the chronic inflammatory type. A moderately thick capsule (generally 120 microns) consisted of a layer of mixed round cells and giant cells along the surface and then a collagen capsule with fibrocytes. Although the inflammatory cells lay directly against the implant surface, the tissues seem to rip off easily during sectioning. Collagen did not touch or even approach the implant.

The twelve-week implants developed a capsule of several (1 to 5) adherent collagen layers all around, with fibrocytes and fibroblasts. The collagen capsule did not have any chronic inflammatory cell separations seen on the two-week implants, but there was a large population of fibroblasts, which normally would have become fibrocytes by twelve-weeks on a more "biocompatible" material. Collagen contact varied from points of contact to continuous contact where the coating of the implant was identifiable. Only a few small blood vessels were seen within the capsule. Pyknotic cells and some fibrous tissue ingrowth were seen inside the surface layer of the implant. There was no collagen seen inside the surface layers of the implants.

COMPARISONS OF RESULTS BETWEEN DIFFERENT MEAN BRIDGING DISTANCES

Comparisons of the histological responses are provided in Table IV in a summarized form.

TABLE IV

| CHARACTERISTIC HISTOLOGICAL RESPONSES TO VARIOUS (MEAN) BRIDGING DISTANCES OF (HYDROPHILIC) VERSAPOR FILTER MATERIAL AFTER TWELVE WEEKS IMPLANTATION IN DOGS | | | | | |
|---|---|---|---|---|---|
| HISTOLOGICAL | MEAN BRIDGING DISTANCE IN MICRONS | | | | |
| PARAMETERS | 0.42 | 1.42 | 1.83 | 3.33 | 3 TO 14 |
| Tissue Capsule: Thickness in microns | 210 | 5 to 25 | 5 to 30 | 115 to 350 | 120 |
| Quality | Granulous | Fibrous | Fibrous | Fibrous | Granulous |
| Surface Contact With: | | | | | |
| Macroph. & Giant Cells | Yes | No | No | Yes Some | Yes |
| Fibroblasts | No | Yes | Yes | Yes | No |
| Collagen | No | Yes | Yes | Yes | No |
| Surface Anchorage | No | Yes | Yes | Yes | No |
| Capsular Contraction | Yes | No | No | No | No |
| Histocompatibility Rating | Poor | Optimal | Optimal | Fair | Poor |
| Manufacturer's Identification | V-200 | V-1200 | V-3000 | V-5000 | V-10,000 |

The main difference between the V-200H material implants and the V-200 implants was that both the connective tissue capsule and the layer of chronic inflammatory cells were noticeably thinner for the V-200H implants. The tissue reactions to the V-200/200H materials were the same as the reaction typically observed to smooth silicone implants, namely, dissipation of inflammatory cells, thinning and contraction of the capsule, and maturation of collagen with extended time. The fact that the tissue reactions to both of these porous materials was so similar to the reactions to smooth implants suggests that if an implant surface has a mean bridging distance of less than 0.5 microns, the tissue reacts as though it were a smooth surface. Namely, the chronic inflammatory reaction produces macrophages which surround the implant in a futile attempt to devour it.

There was very little difference in the tissue reactions to the V-1200, V-1200H, V-3000, and V-3000H materials. All developed extremely thin, adherent connective tissue capsules with minimal inflammatory reaction. All exhibited contact, of varying degree, between collagen and the implant's exterior surface. There was no capsular contraction, as was seen with the implants having mean bridging distances smaller than 0.5 microns. The tissue reactions of the V-1200, V-1200H, V-3000, and V-3000H materials appear to provide excellent implant anchorage in soft tissue. Despite the differences in surface energy, mean bridging distance, and morphology, between the V-1200 and V-1200H, no qualitative differences were observed in the capsules for these two materials. Similarly, the difference in mean bridging distance between the V-1200 and V-3000 implants caused no difference in capsule composition. These observations suggest that the mean bridging distances of these materials fall within a range that is highly acceptable to the connective tissue environment.

The mean bridging distances of the hydrophilic V-5000 and the hydrophobic V-5000H materials were measured to be 3.32 microns and 3.61 microns respectively. At two weeks, implants of these materials developed a fibrous tissue capsule separated from the implant surface by a layer of chronic inflammatory cells, which were primarily giant cells. There was no collagen in contact with the implant, which was seen to have pyknotic cells, red blood cells, macrophages, giant cells, and capillaries within the porosity. At two weeks, the major difference in the reactions was that the hydrophobic implants had thinner capsules than the hydrophilic implants. The V-5000/5000H implants exhibited an inflammatory-cell layer that was more adherent to the surface than that of the V-200/200H material implants.

At twelve weeks, the capsule thickness around the V-5000 implants was reduced slightly, and the inflammatory cells that were observed around the two-week V-5000 implants, were absent. The implants were surrounded by adherent fibrous tissue capsules. Collagen was in continuous contact with the implant, protruding into the surface, and fine strands were observed throughout the implant. This was more evident than on the V-1200 and V-3000 materials implants. However, the same undesirable pyknotic cells, red blood cells, macrophages, giant cells, and capillaries observed inside the two-week V-5000 implants were present in the implants observed at twelve weeks. Apparently, once these undesirable elements penetrate the surface of the implant, they do not leave after twelve weeks.

The reaction of the V-10,000 implant was similar to the reaction to the V-5000/5000H material implants. At two weeks, a fibrous tissue capsule covered a layer of inflammatory cells which had disappeared by twelve weeks. However, the collagen did not protrude into the porosity, as seen with the V-5000/5000H material implants.

In reviewing the results presented by the testing, three different ranges of implant mean bridging distances appear to evoke three different soft tissue responses. The smallest range, which includes mean bridging distances less than 0.5 microns in diameter, evokes the same response as smooth-surfaced implants.

The implants having optimal mean bridging distances ranging from 1.4 to 1.9 microns quickly developed thin, adherent fibrous tissue capsules which remained optimally thin and free of complications for up to twelve weeks, which is a relatively long period of implantation. The hydrophobicity versus hydrophilicity of these implants seems to have very little effect on the nature of the soft tissue response.

The mean bridging distances of 3.3 microns and 3.6 microns becomes infiltrated with granulation tissue and giant cells, which remain permanently. These larger size mean bridging distances initially are surrounded by chronic inflammatory cells, but develop adherent connective tissue capsules after long term implantation. The capsule was thicker and seemed to take longer to stabilize than on the optimal (1.4 to 1.9 micron) mean bridging distance materials. The final anchorage achieved with the larger size mean bridging distance surface, however, may have been better than with the optimal mean bridging distance surface. The collagen fibers of the capsule appeared to protrude into the porosity of the larger size mean bridging distance surface layer, and some collagen fibers were seen inside them.

However, along with the increased anchorage at this larger size, an increase in cellular elements inside the implant also occurred. There was a greater number of pyknotic cells inside the larger size mean bridging distance implants compared to the optimal 1.4 to 1.9 micron mean bridging distance range, and there were giant cells, macrophages, capillaries, and even larger vessels. Although it appeared that firm anchorage had occurred in the larger surface opening size implants, the tissue reaction inside the recess was approaching the granulation tissue observed in implants with larger mean bridging distances It is believed that the ingrowth of giant cells and granulation tissue is to be kept at a minimum.

While it has not been determined at exactly what surface opening size, cells will recognize a change in the surface porosity and react differently, this transition appears to occur at a mean bridging distance smaller than 1.4 microns but larger than 0.5 microns.

It was observed that in the absence of macrophages and giant cells, collagen maturity is improved, and there is a tendency for collagen to adhere to the porous implant surface. It is believed that micro-motion between the implant and the interfacing cells is responsible for the presence of inflammatory cells. Insertion of cytoplasmic projections through surface openings of appropriate size achieved by mechanical cell adhesion may eliminate this micro-motion and result in the absence of inflammatory cells. Mature collagen then develops in the resultant environment. Mechanical stresses also may play a role in the cellular response observed at the implant/tissue interface. Macrophages and giant cells were seen to accumulate in undulations or indentations in the surface of microporous materials which otherwise exhibited adherent collagen layers. It is believed that shear stresses at the implant/tissue interface induce fibrous tissue formation. The absence of stresses within surface openings appears to favor the formation of inflammatory cells. This theory is consistent with the observed tissue reaction to materials with larger mean bridging distances (greater than 10.0 microns).

It is concluded that connective tissue forms and directly adheres to an implant surface in the absence of inflammatory cells. This connective tissue adherence is facilitated by a mean bridging distance of 1.4 to 1.9 microns in the surface of an implant. Results appear to indicate that the connective tissue forms in response to mechanical stresses. In the absence of stresses, such as across large bridging distances and other shielded areas, macrophages and giant cells settle. Because pores of 1.4 to 1.9 microns do not permit cellular ingrowth, the same histocompatibility might be obtained with a surface roughness of the same scale, rather than an interconnecting porosity, although the penetration of collagen fibers into such a porosity may be very desirable. It is believed that the contraction and stiffening associated with smooth-surfaced implants and the persistent inflammatory cell reaction associated with conventional porous implants can be eliminated using the present invention.

It will be apparent to those skilled in the art that various modifications and variations can be made in the present invention without departing from the scope or spirit of the invention. Thus, it is intended that the present invention cover the modifications and variations of this invention provided they come within the scope of the appended claims and their equivalents.

We claim:

1. A soft tissue implant device to be at least partially embedded at an implantation site in organic tissue of a living organism while promoting anchorage of the device at the implantation site and the growth of collagen at the implantation site, without causing encapsulation of the embedded portion of the device and without causing inflammatory tissue at the implantation site, the device comprising:
   (a) a body;
   (b) a surface layer secured to said body and extending over a sufficient portion of said body sot hat only said surface layer contacts the organic tissue at the implantation site;
   (c) said surface layer defining a plurality of three-dimensional features;
   (d) said feature defining an exterior surface for presenting itself to living cells in organic tissue at the implantation site;
   (e) said exterior surface defining a plurality of spaces for presenting themselves to living cells adjacent said exterior surface;
   (f) each said space having a bridging distance being the minimum distance an adjacent cell must stretch to span diametrically across said space, said bridging distance being measured in a direction parallel to said exterior surface at said space;
   (g) said plurality of spaces having a mean bridging distance ranging from greater than 1.0 micron to less than 4.0 microns; and
   (h) wherein said surface layer being produced by casting polymers, which are semifluid and cure over time, onto a surface produced on a glass substrate by selective etching of photoresist spin-coated onto a chrome plated glass plate and which has been exposed to a light image followed by being etched down to the chrome and followed by the chrome being etched down to the glass substrate.

2. A device as in claim 1, wherein:
said bridging distance falls within the range from 1.4 microns to 1.9 microns.

3. A device as in claim 1, wherein:
substantially all of the individual bridging distance measurements are within the ranges of 0.1 to 10.0 microns and 1,000 microns and greater than 1,000 microns.

4. A device as in claim 3, wherein:
said exterior surface having at least one closed perimeter defining a solid surface portion therewithin.

5. A device as in claim 4, wherein:
   (a) said surface layer defines a plurality of projections,
   (b) each said solid surface portion defining the exterior surface of one of said plurality of projections, and
   (c) each said projection being separated by at least one said space from each adjacent projection.

6. A device as in claim 5, wherein:
   (a) each said projection defining a bridging distance relative to each adjacent projection, each said bridging distance being the smallest distance measured in a direction parallel to said exterior surface and separating each said closed perimeter of each said projection from each said closed perimeter of each said adjacent projection;
   (b) each said projection having a breadth dimension, said projection breadth dimension being the smallest diametric dimension measured across said solid surface portion of said projection and measured in a direction parallel to said exterior surface; and
   (c) said plurality of projections having a mean breadth dimension ranging from 0.10 micron to 2.0 microns.

7. A device as in claim 6, wherein:
   (a) said surface layer defines a plurality of recesses, each said space defining an opening to at least one said recess; and
   (b) each said projection having a sidewall defining at least a portion of at least one adjacent recess.

8. A device as in claim 5, wherein:
said plurality of spaces are integral with one another and defines a continuum that separates each said projection from each nearest projection.

9. A device as in claim 1, wherein:
said surface layer is integral with said body.

10. A soft tissue implant device to be at least partially embedded at an implantation site in organic tissue of a living organism while promoting anchorage of the device at the implantation site and the growth of collagen at the implantation site, without causing encapsulation of the embedded portion of the device and without causing inflammatory tissue at the implantation site, the device comprising:
   (a) a body;
   a surface layer secured to said body and extending over a sufficient portion of said body so that only said surface layer contacts the organic tissue at the implantation site;
   (c) said surface layer defining a plurality of three-dimensional features;
   (d) said features defining an exterior surface for presenting itself to living cells in organic tissue at the implantation site;
   (e) said exterior surface defining a plurality of solid surface portions, each said surface portion being bounded in said exterior surface by a closed perimeter;
   (f) a plurality of said surface layer features defining, respectively, a plurality of projections, and each said solid surface portion defining the exterior surface of one of said plurality of projections;

(g) a plurality of spaces defined in said exterior surface and separating each said solid surface portion from each adjacent solid surface portion;

(h) a plurality of bridging distances defined between each said closed perimeter of each said exterior surface portion and each closed perimeter of each adjacent surface portion, each said bridging distance being the minimum diametric distance an adjacent cell must stretch to span between the closest point on the perimeter of each exterior surface portion and the perimeter of each adjacent exterior surface portion, each said bridging distance being measured in a direction parallel to said exterior surface at said exterior surface portions at each end of said bridging distance;

(i) said plurality of exterior surface portions having a mean bridging distance ranging from greater than 1.0 micron to less than 4.0 microns;

(j) each said projection having a breadth dimension, said projection breadth dimension being the smallest diametric dimension of said exterior surface portion measured across said solid surface portion and in a direction parallel to said exterior surface;

(k) said plurality of projections having a mean breadth dimension ranging from 0.10 micron to 2.0 microns; and (l) wherein said surface layer being produced by casting polymers, which are semifluid and cure over time, onto a surface produced on a glass substrate by selective etching of photoresist spin-coated onto a chrome plated glass plate and which has been exposed to a light image followed by being etched down to the chrome and followed by the chrome being etched down to the glass substrate.

* * * * *